United States Patent
Bremer

(10) Patent No.: US 11,052,158 B2
(45) Date of Patent: Jul. 6, 2021

(54) DELIVERY OF UREA TO CELLS OF THE MACULA AND RETINA USING LIPOSOME CONSTRUCTS

(71) Applicant: Troy Bremer, Irvine, CA (US)

(72) Inventor: Troy Bremer, Irvine, CA (US)

(*) Notice: Subject to any disclaimer, the term of this patent is extended or adjusted under 35 U.S.C. 154(b) by 0 days.

(21) Appl. No.: 16/326,195

(22) PCT Filed: Aug. 18, 2017

(86) PCT No.: PCT/US2017/047643
§ 371 (c)(1),
(2) Date: Feb. 16, 2019

(87) PCT Pub. No.: WO2018/035476
PCT Pub. Date: Feb. 22, 2018

(65) Prior Publication Data
US 2019/0184030 A1    Jun. 20, 2019

Related U.S. Application Data

(60) Provisional application No. 62/376,862, filed on Aug. 18, 2016.

(51) Int. Cl.
| | | |
|---|---|---|
| *A61K 9/127* | (2006.01) | |
| *A61K 31/17* | (2006.01) | |
| *A61K 47/69* | (2017.01) | |
| *A61K 9/00* | (2006.01) | |
| *A61P 27/02* | (2006.01) | |

(52) U.S. Cl.
CPC ........ *A61K 47/6911* (2017.08); *A61K 9/0019* (2013.01); *A61K 9/0048* (2013.01); *A61K 9/127* (2013.01); *A61K 9/1271* (2013.01); *A61K 31/17* (2013.01); *A61K 47/6917* (2017.08); *A61P 27/02* (2018.01)

(58) Field of Classification Search
CPC .. A61K 9/127; A61K 47/6911; A61K 9/1271; A61K 47/6917; A61K 9/0019; A61K 31/17; A61K 9/0048; A61K 9/107; A61K 47/18; A61K 47/28; A61P 27/02
See application file for complete search history.

(56) References Cited

U.S. PATENT DOCUMENTS

| | | | |
|---|---|---|---|
| 4,394,149 A | | 7/1983 | Szoka et al. |
| 4,839,175 A | * | 6/1989 | Guo ........... A61K 9/127 264/4.3 |
| 4,954,345 A | | 9/1990 | Muller |
| 5,077,057 A | * | 12/1991 | Szoka, Jr. ...... A61K 9/1277 264/4.1 |
| 5,629,344 A | | 5/1997 | Charlton et al. |

(Continued)

OTHER PUBLICATIONS

Tabandeh, H., et al in DARU Journal of Pharmaceutical Science, vol. 9, # 1-2, pp. 28-32, 2001.*

(Continued)

*Primary Examiner* — Gollamudi S Kishore
(74) *Attorney, Agent, or Firm* — Grimes & Yvon LLP

(57) ABSTRACT

Provided are liposome constructs for delivery of urea to the vitreoretinal interface of the eye. The liposome constructs are agglomerates of small lamellar vesicles (SUVs) and have a greater density than the vitreal fluid, such that they sink to the back of the eye rather than dispersing throughout the vitreous.

18 Claims, 19 Drawing Sheets

(56) References Cited

U.S. PATENT DOCUMENTS

| | | | |
|---|---|---|---|
| 5,811,118 A | 9/1998 | Ostro et al. | |
| 5,843,473 A * | 12/1998 | Woodie | A61K 9/1271 |
| | | | 424/450 |
| 5,885,260 A | 3/1999 | Mehl et al. | |
| 8,956,600 B2 | 2/2015 | Shih et al. | |
| 2008/0171795 A1 * | 7/2008 | Katare | A61K 9/06 |
| | | | 514/738 |
| 2012/0196937 A1 * | 8/2012 | Karageozian | A61K 31/155 |
| | | | 514/588 |
| 2013/0259922 A1 | 10/2013 | Haas et al. | |
| 2014/0050780 A1 | 2/2014 | Cerundolo et al. | |
| 2014/0271822 A1 | 9/2014 | McGhee et al. | |
| 2015/0038464 A1 * | 2/2015 | Jensen | A61K 31/436 |
| | | | 514/89 |
| 2016/0022763 A1 | 1/2016 | Mackel et al. | |
| 2016/0101178 A1 * | 4/2016 | Wilson | A61K 47/06 |
| | | | 514/29 |
| 2016/0256387 A1 * | 9/2016 | Zhu | A61K 9/0019 |
| 2018/0161291 A1 * | 6/2018 | McGovern | A61P 27/02 |

OTHER PUBLICATIONS

Wang, Z., et al in World J. Surg Oncol, vol. 11, p. 300, 2013.*
Visudyne Package Insert, Bausch & Lomb Inc., Revised Feb. 2017.
Srinivas, et al. Formulation and Evaluation of Parenteral Methotrexate Nanoliposomes, Int'l J. Pharm. Pharm. 6(11):295-300 (2014).

* cited by examiner

C

D

A

B

C

A

B

A

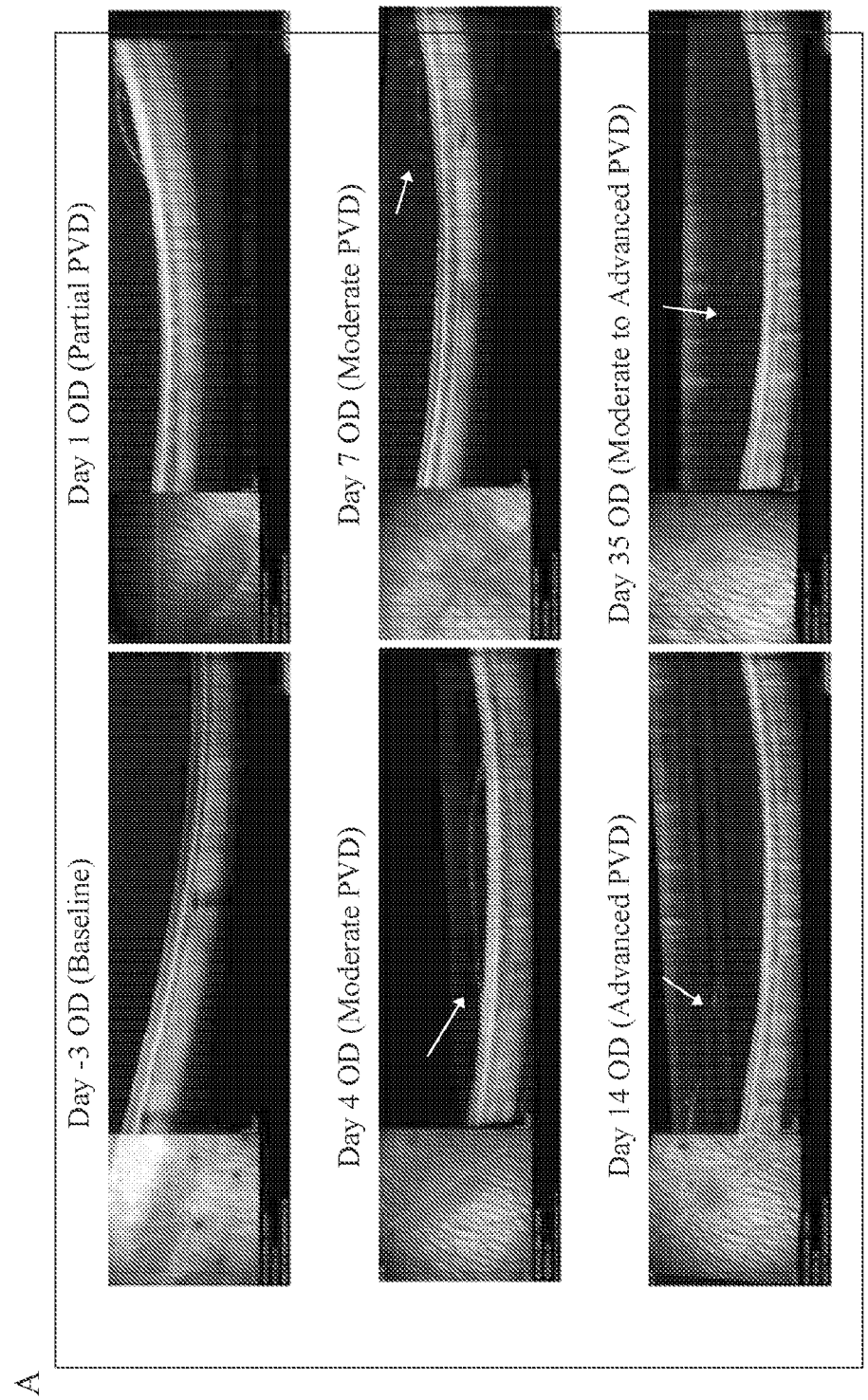

DELIVERY OF UREA TO CELLS OF THE MACULA AND RETINA USING LIPOSOME CONSTRUCTS

CROSS-REFERENCE TO RELATED APPLICATIONS

This application is the National Stage of International Application No. PCT/US2017/047643, filed on Aug. 18, 2017, and claims the benefit of U.S. Provisional Application No. 62/376,862, filed Aug. 18, 2016, the entire contents of both of which are incorporated herein by reference in their entirety for all purposes.

BACKGROUND

The eye is a very active organ with a constant high-volume circulation of blood and other fluids in and around the globe. The retina is a layer of nerves that lines the back of the eye and contains specialized photoreceptor cells, called rods and cones, which sense light. The retina sends light signals to the visual cortex of the brain through the optic nerve. Cone cells are most concentrated in a small area of the retina called the macula. The choroid is a highly vascular structure between the retina and the white outer layer of the eye, the sclera. The choroid acts as both a source of oxygen and nutrients to the retina, as well as a drainage system of the aqueous humor from the anterior chamber. The eye is filled with a gel-like substance called the vitreous or vitreous body. The vitreous body is an orb-shaped structure of mostly water with a significant concentration of hyaluronan and collagen, plus lesser amounts of a variety of other proteins. The posterior portion of the vitreous body is in direct contact with the retina. Networks of fibrillar strands extend from the retina and insert into the vitreous body to attach it to the retina. See Sebag, *Graefe's Arch. Clin. Exp. Ophthalmol.* 225:89-93 (1987).

The standard administration of currently approved drugs for pathologies of the retina is intra-vitreal injection of a 100 microliter dose using a 26-30 gauge needle, delivered through a structure in the middle layer of the eye, the pars plana, and released in the central portion of the vitreous. It has been established by pharmacokinetic analysis that drugs injected into the vitreous dissipate within a few hours to outer tissues of the eye and are totally removed after 24 hours. The typical 100 microliter injection is diluted by a factor of 50 to 1 before a small concentration moves to the area of prime interest, the macula.

Because the volume of drug that can be delivered to the eye is limited by the size of the organ, and because ophthalmic formulations dissipate relatively quickly once introduced into the vitreous, delivering and maintaining therapeutic doses of drugs to the macula and adjacent tissues has been a great challenge for ophthalmic drug developers and clinicians. There exists a need for ophthalmic drug formulations that can deliver a therapeutically effective dose, particularly of a highly water-soluble active agent such as urea, to the back of the eye over an extended period for the treatment of chronic diseases, such as, for example, diabetic retinopathy.

SUMMARY OF EMBODIMENTS OF THE INVENTION

Some of the main aspects of the embodiments of the present invention are summarized below. Additional aspects are described in the Detailed Description of Embodiments of the Invention, Examples, Drawings, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the present invention.

This disclosure provides a pharmaceutical composition comprising a liposome construct and a pharmaceutically acceptable carrier, wherein the liposome construct comprises an agglomerate of small unilamellar vesicles (SUVs), wherein the SUVs comprise urea encapsulated within the SUVs, wherein the SUVs have a specific gravity that is greater than about 1.05, a z-average diameter of less than about 220 nm, and a polydispersity index value (PdI) of less than about 0.30. In some embodiments, the z-average diameter is less than about 200 nm. The pharmaceutically acceptable carrier can optionally comprise urea.

In one embodiment, the pharmaceutical composition is in the form of an emulsion or a suspension.

The SUVs have a lipid bilayer (i.e., a lamella) that surrounds a central compartment. In one aspect, the lamella comprises one or more phospholipids and no cholesterol. In another aspect, the lamella comprises (i) one or more phospholipids and (ii) less than about 70 mol % cholesterol, or 1-9 mol % cholesterol, or 34-69 mol % cholesterol, or 42-69 mol % cholesterol, or 10-20 mol % cholesterol, or 20-30 mol % cholesterol, or 30-40 mol % cholesterol, or 40-50 mol % cholesterol, or 50-60 mol % cholesterol, or 60-69 mol % cholesterol. In certain embodiments, the lamella comprises one or more of cholesterol, dioleoyl phosphatidylcholine (DOPC), dioleyl phosphatidylethanolamine (DOPE), dioleoyl trimethylammonium propane (DOTAP), dipalmitoyl phosphatidylcholine (DPPC), dipalmitoyl phosphatidylglycerol (DPPG), distearoyl phosphatidylcholine (DSPC), phosphatidylcholine (PC), and palmitoyl oleoyl phosphatidylcholine (POPC).

In particular embodiments, the lamella consists essentially of 58 mol % DPPC and 42 mol % cholesterol; 58 mol % DOPC and 42 mol % cholesterol; 58 mol % POPC and 42 mol % cholesterol; 29 mol % DPPC, 42 mol % cholesterol, and 29 mol % DPPG; 80 mol % POPC and 20 mol % DOTAP; 67 mol % DMPC and 33 mol % DMPG; or 33 mol % DPPC, 13 mol % DSPC, 32 mol % DOPC, 17 mol % 18:2 PC, 5 mol % 20:4 PC. In a preferred embodiment, the lamella consists essentially of 58 mol % DOPC and 42 mol % cholesterol.

In certain aspects, the SUVs comprise a surface modifying group such as polyethylene glycol (PEG).

The SUVs can have an encapsulation efficiency of at least about 10%, 15%, 20%, 25%, 30%, 35%, 40%, 45%, 50%, 55%, 60%, 65%, 70%, 75%, 80%, 85%, or 90%. In some embodiments, the SUVs have an encapsulation efficiency of at least about 20%.

In some embodiments, a packed pellet of the SUVs comprises at least about 0.1 mg, and preferably at least about 0.2 mg, 0.25 mg, 0.3 mg, 0.35 mg, 0.4 mg, 0.45 mg, or 0.5 mg of encapsulated urea per microliter of packed pellet. The amount of encapsulated urea will depend upon the desired dosage for delivery.

Also provided is a method for delivering urea to the vitreoretinal interface, the method comprising administering to the vitreous of a subject a pharmaceutical composition of the invention.

One embodiment is directed to a method of inducing posterior vitreous detachment (PVD) in a subject having or susceptible to disease or disorder of the eye that can be treated or prevented by inducing PVD, the method comprising administering to the vitreous of the subject a pharmaceutical composition comprising the liposome construct of the invention. In particular embodiments, the disease or disorder can be, for example, diabetic retinopathy or vitreomacular adhesion (VMA).

Further provided is a method of treating diabetic retinopathy or VMA in a subject, the method comprising administering to the vitreous of the subject a pharmaceutical composition of the invention.

The methods of the invention can comprise administration of the pharmaceutical composition of the invention by intravitreal injection. In one embodiment, intravitreal injection is through the pars plana. The methods of the invention can comprise administration wherein the subject is in a supine position.

Specific embodiments provide release characteristics of the liposome constructs. In some aspects, at least 80% of the urea is released from the liposome construct within 24 hours after administration. In some aspects, at least 80% of the urea is released from the liposome construct within 8 hours after administration. In some aspects, at least 80% of the urea is released from the liposome construct within 4 hours after administration.

Embodiments of the invention include the use of a liposome construct or composition of the invention to induce posterior vitreous detachment (PVD) or to treat or prevent a disease or disorder of the eye that can be treated or prevented by inducing PVD. One embodiment of the invention includes the use of a pharmaceutical composition comprising a liposome construct of the invention to treat or prevent diabetic retinopathy or vitreomacular adhesion (VMA).

An additional aspect is a kit comprising a liposome construct or pharmaceutical composition of the invention.

BRIEF DESCRIPTION OF THE DRAWINGS

(FIG. 3A), room temperature (FIG. 3B), or 37° C. (FIG. 3C).

FIG. 12A shows graphs of dark-adapted control (upper panels) and Group 8 (lower panels) animals exposed to blue light. FIG. 12B shows graphs of dark-adapted control (upper panels) and Group 8 (lower panels) animals exposed to red light.

DETAILED DESCRIPTION OF EMBODIMENTS OF THE INVENTION

Figure 1:
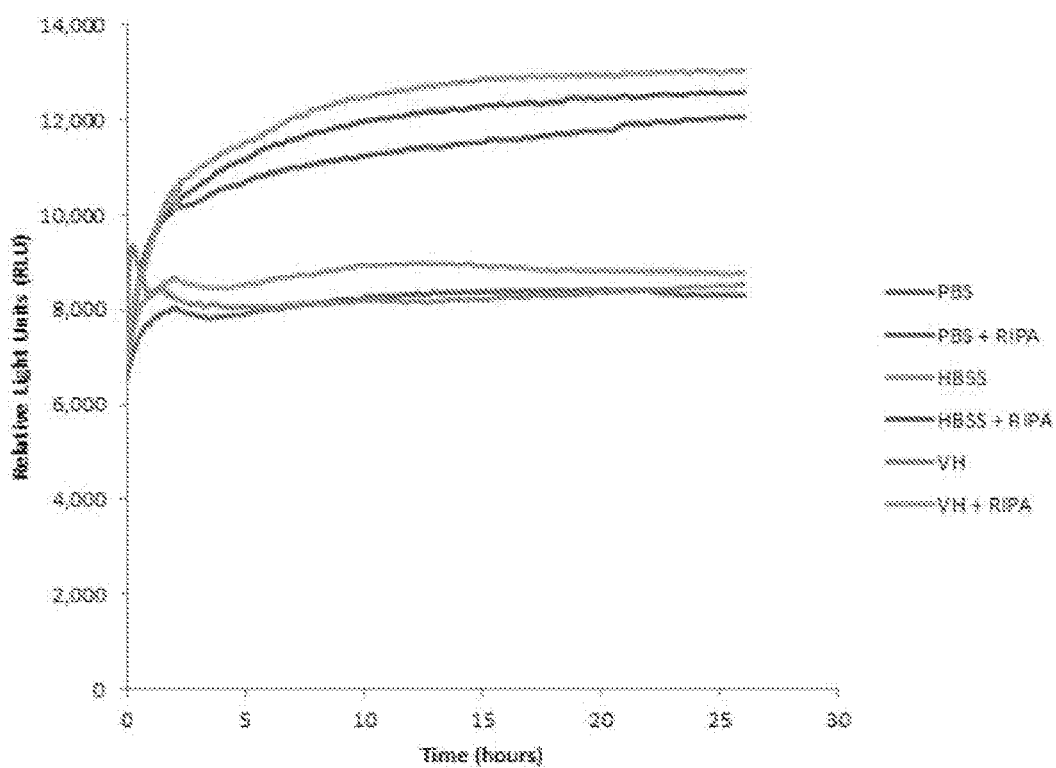
FIGS. 1A-1E show carboxyfluorescein leakage over a 24-hour period from intact and lysed liposome constructs made from Formulation 1 (as disclosed herein) (FIG. 1A), Formulation 3 (as disclosed herein) (FIG. 1B), Formulation 8 (as disclosed herein) (FIG. 1C), Formulation 11 (as disclosed herein) (FIG. 1D), or Formulation 12 (as disclosed herein) (FIG. 1E). Formulations are described in Table 1.
Figure 1:
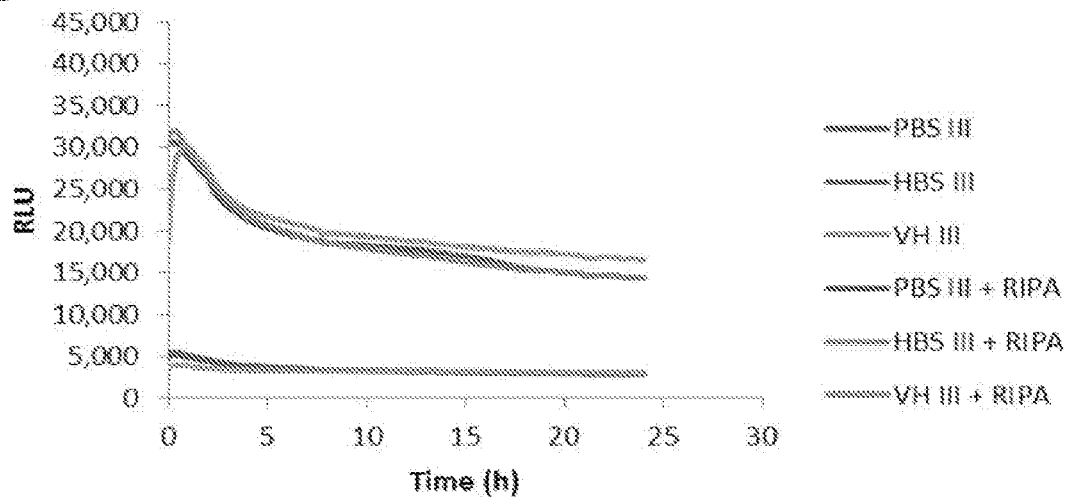
Figure 1:
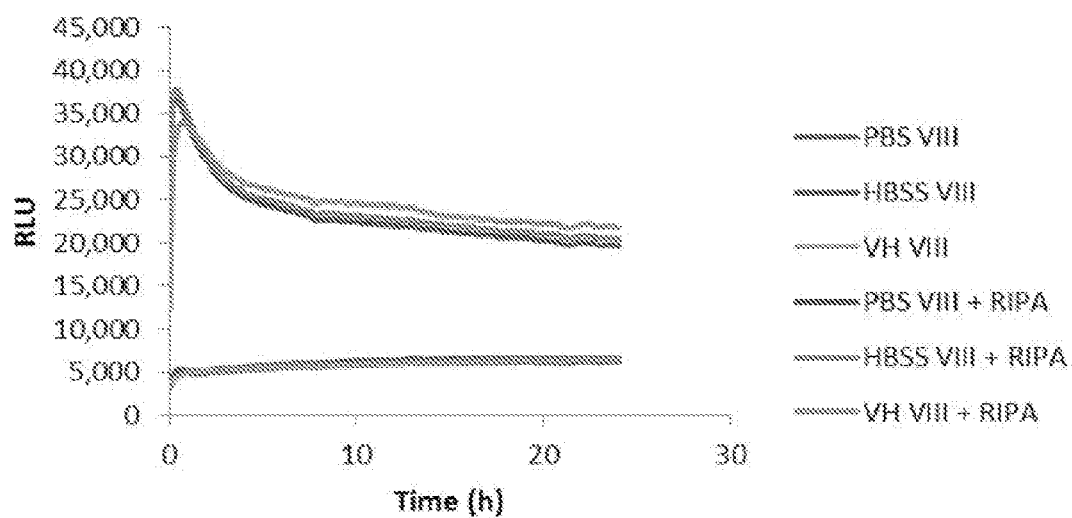
Figure 1:
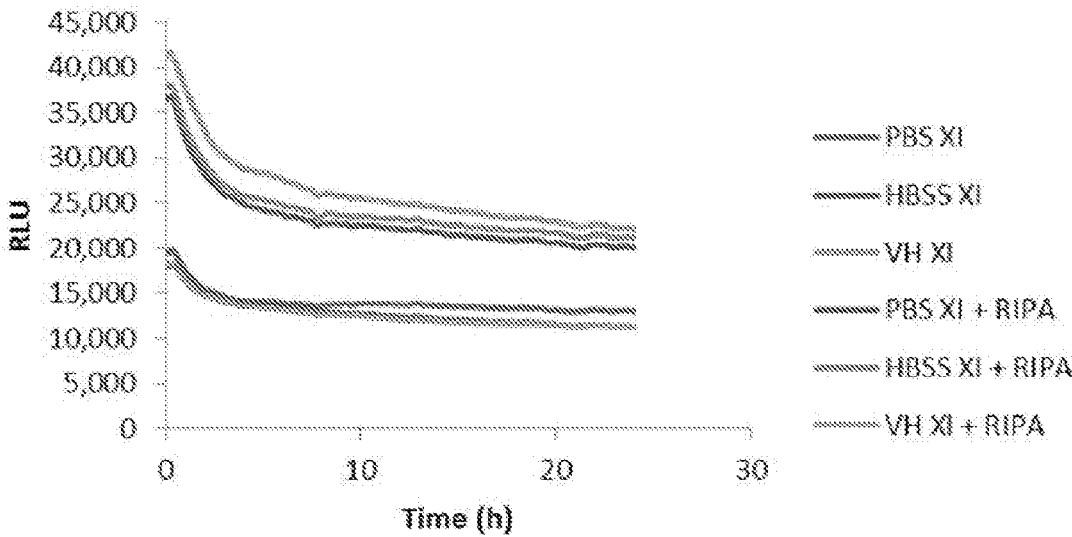
Figure 1:
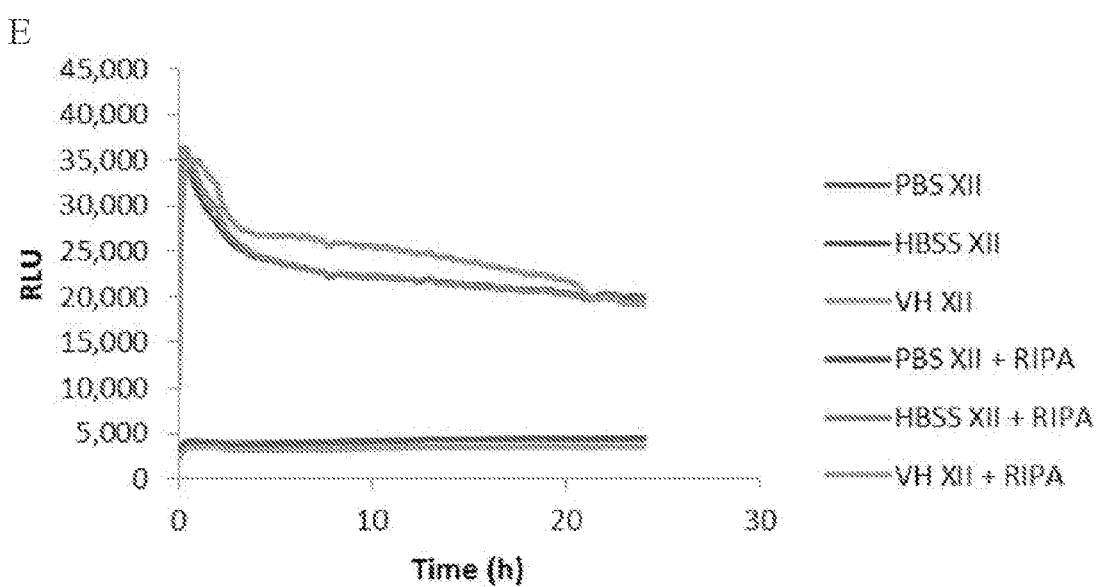
Figure 2:
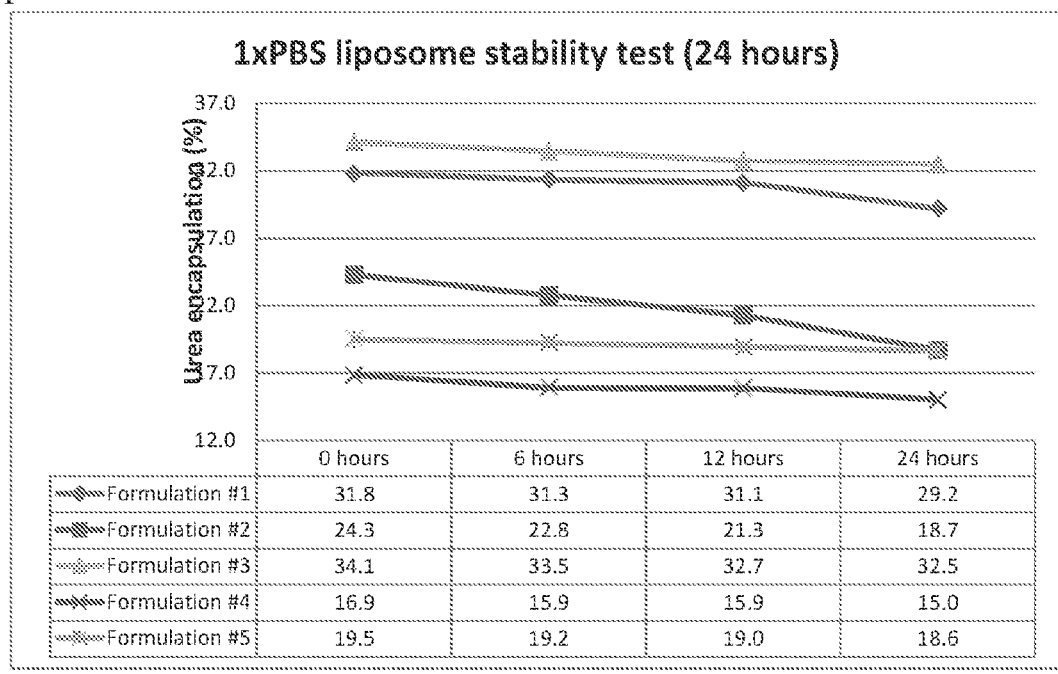
FIG. 2A-2D show stability over a 24-hour period of urea-encapsulated liposome constructs in 1× PBS (FIG. 2A, 2B) or rabbit vitreous humor (FIG. 2C, 2D). Formulations #1, #2, #3, #4, and #5 in the graphs correspond, respectively, to Formulations 1, 2, 3, 12, and 14 described in Table 1.
Figure 2:
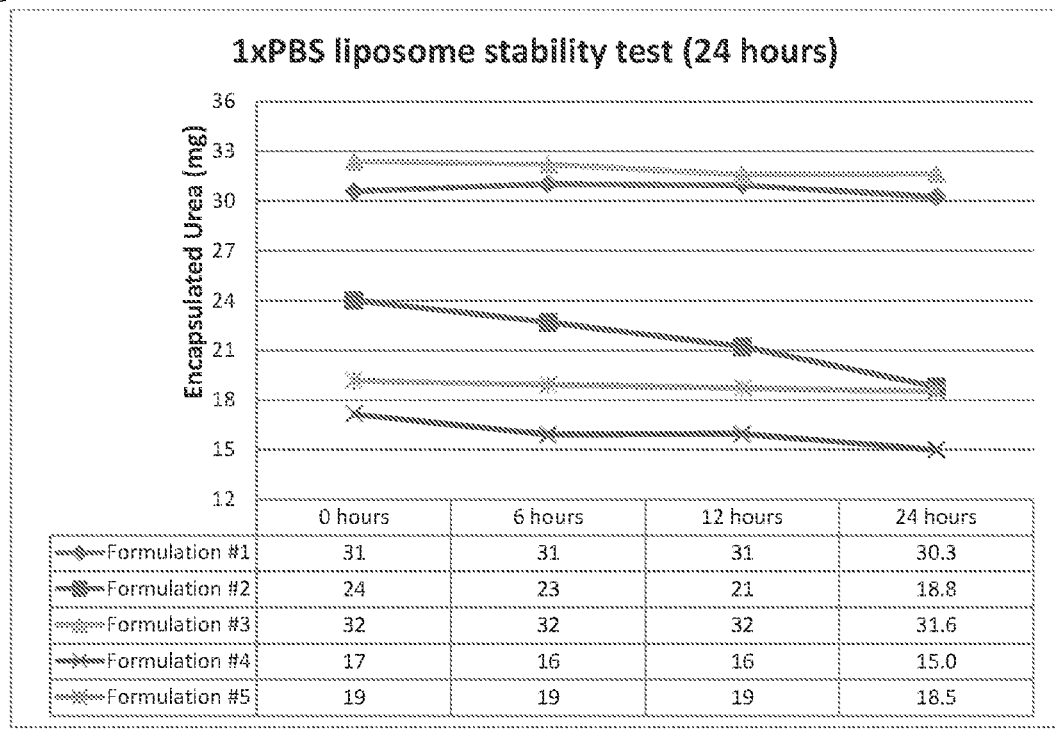
Figure 2:
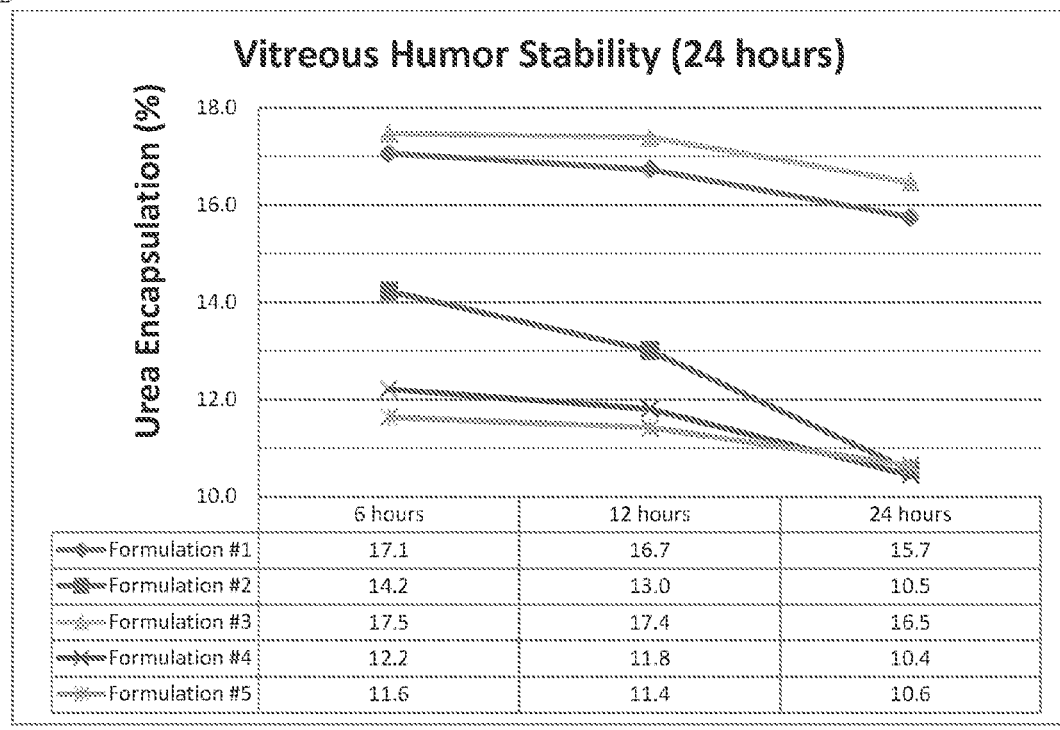
Figure 2:
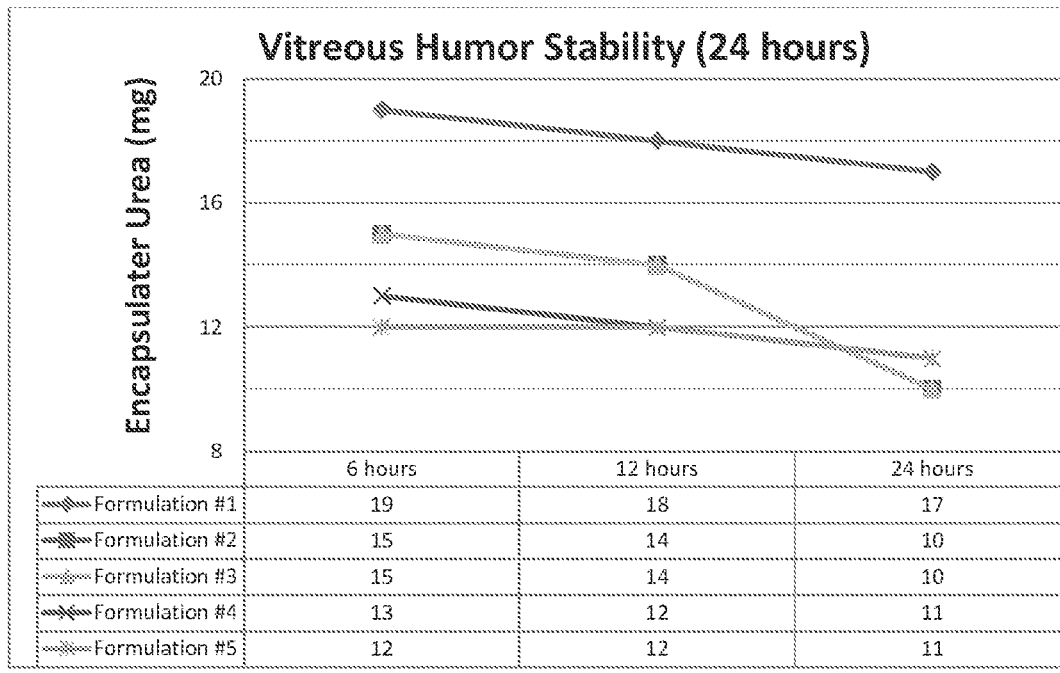

Embodiments of the present invention provide novel formulations for delivery of urea to the retina and macula. The liposome constructs of the embodiments of the invention can selectively and specifically release urea at the target area within the eye to treat, prevent, diagnose, and/or monitor a disease or disorder of the eye.

The practice of the embodiments of the present invention will employ, unless otherwise indicated, conventional techniques of pharmaceutics, formulation science, protein chemistry, cell biology, cell culture, molecular biology, transgenic biology, microbiology, recombinant DNA, and immunology, which are within the skill of the art. Such techniques are explained fully in the literature. See, e.g., *Handbook of Pharmaceutical Excipients* (7th ed., Rowe et al. eds., 2012); *Martin's Physical Pharmacy and Pharmaceutical Sciences* (6th ed., Sinko, 2010); *Remington: The Science and Practice of Pharmacy* (21st ed., Univ. Sci. Philadelphia ed., 2005); *Current Protocols in Molecular Biology* (Ausubel et al. eds., 2016); *Molecular Cloning: A Laboratory Manual* (4th ed., Green and Sambrook eds., 2012); *Lewin's Genes XI* (11th ed., Krebs et al. eds., 2012); *DNA Cloning: A Practical Approach, Volumes I and II* (2d ed., Glover and Hames eds., 1995); *Protein Engineering: A Practical Approach* (1st ed., Rees et al. eds. 1993); *Culture Of Animal Cells* (6th ed. Freshney, 2010); *Antibodies: A Laboratory Manual* (2nd ed., Greenfield ed., 2013); *Antibody Engineering* (2d ed., Borrebaeck ed., 1995).

In order that the embodiments of the present invention can be more readily understood, certain terms are first defined. Additional definitions are set forth throughout the disclosure. Unless defined otherwise, all technical and scientific terms used herein have the same meaning as commonly understood by one of ordinary skill in the art to which this invention is related. For example, *Dictionary of Pharmaceutical Medicine* (3rd ed. Nahler and Mollet eds., 2013); *The Dictionary of Cell and Molecular Biology* (5th ed. J. M. Lackie ed., 2013), *Oxford Dictionary of Biochemistry and Molecular Biology* (2d ed. R. Cammack et al. eds., 2008), and *The Concise Dictionary of Biomedicine and Molecular Biology* (2d ed. P-S. Juo, 2002) can provide one of skill with general definitions of some terms used herein.

Any headings provided herein are not limitations of the various aspects or embodiments of the invention, which can be had by reference to the specification as a whole. Accordingly, the terms defined immediately below are more fully defined by reference to the specification in its entirety.

I. Definitions

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Wherever embodiments are described with the language "comprising," otherwise analogous embodiments described in terms of "consisting of" and/or "consisting essentially of" are included.

Units, prefixes, and symbols are denoted in their Système International de Unites (SI) accepted form. Numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth. Unless otherwise indicated, amino acid sequences are written left to right in amino to carboxy orientation, and nucleic acid sequences are written left to right in 5' to 3' orientation. Amino acids are referred to by their commonly known three-letter symbols or by the one-letter symbols recommended by the IUPAC-IUB Biochemical Nomenclature Commission. Nucleotides, likewise, are referred to by their commonly accepted single-letter codes.

A "liposome" is a spherical vesicle with a lipid bilayer surrounding a central compartment. Liposomes can be classified on the basis of the structure of the lipid bilayer. Unilamellar vesicles have one bilayer surrounding the central compartment, while multilamellar vesicles (MLVs) have more than one bilayer surrounding the central compartment. Liposomes can also be classified on the basis of size: small unilamellar vesicles (SUVs) are typically about 20-100 nm in diameter; large unilamellar vesicles (LUVs) are typically greater than 100 nm in diameter; and giant unilamellar vesicles (GUVs) are typically greater than about 250 nm in diameter. MLVs are typically about 100-500 nm in diameter.

The "encapsulation efficiency" is the percentage of an active agent that is entrapped within a washed pellet of liposomes, relative to the active agent in the supernatant, calculated by the following equation:

$$\text{Encapsulation \%} = 100 \times [(\text{amount of active agent encapsulated})/(\text{initial amount of active agent in loading solution})]$$

Encapsulation efficiency can be calculated based on weight, volume, or concentration.

The "percent encapsulated" is $100 \times [(\text{amount of active agent encapsulated})/(\text{total amount of active agent})]$.

As used herein, a "liposome construct" is a particle comprising an agglomerate of SUVs. The liposome constructs of the invention are individual SUVs that self-assemble into liposome constructs, which are denser than the vitreous of the eye. Without wishing to be bound by theory, the individual SUVs are held together by intermolecular forces characterized by charge-sharing. Unexpectedly, the liposome constructs maintain their globular, gel-like structure once administered, such that they do not disperse or break apart during delivery throughout the vitreous body, but instead can sink through the vitreous and blanket the retina. The liposome constructs can comprise an emulsifier or binding agent to enhance agglomeration. The liposome constructs can comprise a surface group (for example, PEG) that facilitates direct or indirect secondary binding between SUVs, which can be hydrolyzed under certain conditions, such as a change in pH.

Particle size can be expressed as a "z-average diameter," which is the mean diameter based upon the intensity of scattered light. The "polydispersity index (PdI)" is an estimate of the width of the particle size distribution. Particle size distribution in a sample can also be expressed in "D-values," which are based on percentage mass of particles in the sample. The "D90" is the diameter at which 90% of a sample's mass is comprised of smaller particles. The "D50" is the diameter at which 50% of a sample's mass is comprised of smaller particles. The "D10" is the diameter at which 10% of a sample's mass is comprised of smaller particles.

As used herein, the terms "vitreous," "vitreous body," "vitreous humor," and "vitreal fluid," are used interchangeably to refer to the gelatinous material that occupies approximately four-fifths of the cavity of the eyeball, behind the lens. The posterior portion of the vitreous is in direct contact with the retina in a region called the "vitreoretinal interface." The density of the liposome constructs permits targeted delivery of urea to the vitreoretinal interface, and reduces the possibility that the urea will negatively affect other regions of the eye.

An "isolated" molecule, e.g., an isolated polypeptide or an isolated polynucleotide, is one that is in a form not found in nature, including those which have been purified. In some embodiments, an isolated molecule is substantially pure. As used herein, the term "substantially pure" refers to purity of greater than 75%, preferably greater than 80% or 90%, and most preferably greater than 95%.

A "label" is a detectable compound that can be conjugated directly or indirectly to a molecule, so as to generate a "labeled" molecule. The label can be detectable on its own (e.g., radioisotope labels or fluorescent labels) or can catalyze chemical alteration of a substrate compound or composition that is detectable (e.g., an enzymatic label).

The terms "inhibit," "block," and "suppress" are used interchangeably and refer to any statistically significant decrease in biological activity, including full blocking of the activity. For example, "inhibition" can refer to a decrease of at least about 10%, 20%, 30%, 40%, 50%, 60%, 70%, 80%, 90% or 100% in biological activity.

The terms "active agent," "therapeutic agent," and "drug" are used interchangeable to refer to any substance, other than food, used in the prevention, diagnosis, alleviation, treatment, or cure of a disease. Active agents include protective agents and diagnostic agents. The active agent can include any substance disclosed in at least one of: The Merck Index, 15th Edition (2013); Pei-Show Juo, Concise Dictionary of Biomedicine and Molecular Biology, (2001); U.S. Pharmacopeia Dictionary of USAN & International Drug Names (2014); and Physician's Desk Reference, 70th Edition (2016). See also Stedman's Medical Dictionary, 28th Edition (2013).

The term "pharmaceutical composition" refers to a preparation in which the active agent is in an effective form, i.e., is biologically active and is formulated such that it can be released in an environment and at a concentration that engenders a therapeutic effect, and which contains no additional components that are unacceptably toxic to a subject to which the composition would be administered. Such a composition can be sterile and can comprise a pharmaceutically acceptable carrier, such as physiological saline. Suitable pharmaceutical compositions can comprise one or more of a buffer (e.g. acetate, phosphate or citrate buffer), a surfactant (e.g. polysorbate), a stabilizing agent (e.g. human albumin), a preservative (e.g. benzyl alcohol), an absorption promoter to enhance bioavailability, and/or other conventional solubilizing or dispersing agents.

A "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and laboratory animals including, e.g., humans, non-human primates, canines, felines, porcines, bovines, equines, rodents, including rats and mice, rabbits, etc.

An "effective amount" of an active agent is an amount sufficient to carry out a specifically stated purpose. An "effective amount" can be determined empirically and in a routine manner, in relation to the stated purpose.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already with the disorder. In certain embodiments, a subject is successfully "treated" for a disease or disorder of the eye according to the methods provided herein if the patient shows, e.g., total, partial, or transient alleviation or elimination of symptoms associated with the disease or disorder.

"Prevent" or "prevention" refer to prophylactic or preventative measures that prevent and/or slow the development of a targeted pathologic condition or disorder. Thus, those in need of prevention include those prone to have or susceptible to the disorder. In certain embodiments, a disease or disorder of the eye is successfully prevented according to the methods provided herein if the patient develops, transiently or permanently, e.g., fewer or less severe symptoms associated with the disease or disorder, or a later onset of symptoms associated with the disease or disorder, than a patient who has not been subject to the methods of the invention.

II. Liposome Constructs

Liposomes that are subunits of the liposome constructs of embodiments of the present invention are SUVs composed of a core enclosed by a bilayer of natural or synthetic origin. The liposomes can comprise one or a mixture of more than one phospholipid. The phospholipids can have different chain lengths, different charges, and can be saturated or unsaturated. Incorporation of cholesterol enhances the stability of liposomes by improving the rigidity of the membrane. In some embodiments, the liposomes can utilize cholesterol and lipid-conjugated hydrophilic polymers as the main components. The choice of components and their relative ratios influence the structural stability of the liposomes, their release time, the amount of cargo (i.e., urea) encapsulated, and the process used for encapsulation.

In particular, the liposome subunits can comprise one or more of: cholesterol, diarachidonoyl phosphatidylcholine (DAPC), dibehenoyl phosphatidylcholine (DBPC), dilauroyl phosphatidylcholine, (DLPC), dimyristoyl phosphatidic acid (DMPA), dimyristoyl phosphatidylcholine (DMPC), dimyristoyl phosphatidylglycerol (DMPG), dimyristoyl phosphatidylinositol (DMPI), dimyristoyl phosphatidylserine (DMPS), dioleoyl phosphatidic acid (DOPA), dioleoyl phosphatidylcholine (DOPC), dioleyl phosphatidylethanolamine (DOPE), dioleoyl phosphatidylglycerol (DOPG), dioleoyl phosphatidylinositol (DOPI), dioleoyl phosphatidylserine (DOPS), dioleoyl trimethylammonium propane (DOTAP), dipalmitoyl phosphatidic acid (DPPA), dipalmitoyl phosphatidylcholine (DPPC), dipalmitoyl phosphatidylcholine-phosphatidylcholine (DPPC-PC), dipalmitoyl phosphatidylethanolamine (DPPE), dipalmitoyl phosphatidylglycerol (DPPG), dipalmitoyl phosphatidylinositol (DPPI), dipalmitoyl phosphatidylserine (DPPS), distearoyl phosphatidic acid (DSPA), distearoyl phosphatidylcholine (DSPC), monosialoganglioside, distearoyl phosphatidylethanolamine (DSPE), distearoyl phosphatidylinositol (DSPI), distearoyl phosphatidylserine (DSPS), egg phosphatidylcholine (EPC), hydrogenated egg phosphatidylcholine (HEPC), hydrogenated phosphatidylcholine (HPC), hydrogenated soy phosphatidylcholine (HSPC), monooleoyl phosphatidylethanolamine (MOPE), myristoyl palmitoyl phosphatidylcholine (MPPC), phosphatidic acid (PA), phosphatidylcholine (PC), phosphatidylethanolamine (PE), phosphatidylglycerol (PG), phosphatidylinsitol (PI), palmitoyl oleoyl phosphatidylcholine (POPC), phosphatidylserine (PS), palmitoyl stearoyl phosphatidylcholine (PSPC), palmitoyl stearoyl phosphatidylglycerol (PSPG), soy phosphatidylcholine (SPC), sphingomyelin (SPM), and/or polyethylene glycol (PEG)-conjugated derivatives of the foregoing. Chang et al., *Int'l J. Nanomed.* 7:49-60 (2012) discloses a number of lipid structures in liposomal formulations. Preferred formulations of the invention are provided in Table 1.

The size of the SUVs is critical. The SUVs preferably have a z-average diameter of between about 50 nm and about 250 nm, preferably between about 140-220 nm, or about 100-200 nm, or about 120-190 nm, or about 150-200 nm, or about 160-180 nm, or about 165-200 nm, as measured by dynamic light scattering. Ideally, the SUVs have a relatively narrow size distribution. In some embodiments, the PdI is between about 0.02 and 0.30. In some embodiments, the PdI is less than about 0.30, 0.25, 0.20, 0.15, 0.125, 0.10, or 0.050. In some embodiments, 90% of SUVs in a sample have a diameter of less than about 300 nm, about 270 nm, about 250 nm, or about 220 nm. In some embodiments, 10% of SUVs have a diameter of less than about 120 nm, about 100 nm, about 50 nm, about 20 nm, or about 10 nm, as measured by dynamic light scattering. Preferably, 90%, 95%, or 100% of the SUVs in a sample have a diameter of less than about 250 nm, or less than about 200 nm, or less than about 175 nm, or less than about 150 nm, as measured by dynamic light scattering.

The SUVs comprise urea encapsulated within them, i.e., the urea is "cargo" in the central compartment of the SUVs.

The SUVs of the various embodiments of the present invention have a specific gravity that is greater than that of vitreous humor. In a preferred embodiment, the SUVs have a specific gravity that is greater than about 1.05, about 1.06, about 1.07, about 1.08, about 1.09, about 1.1, about 1.15, or about 1.2.

Zeta potential measures the electrostatic repulsion between particles of similar charge in a dispersion or solution. The magnitude of the zeta potential indicates the degree of electrostatic repulsion between adjacent, similarly charged particles. When zeta potential is low, attractive forces between particles can exceed repulsive forces, resulting in more agglomeration. When zeta potential is high, the particles resist aggregation. In some embodiments, the SUVs have a zeta potential of between about −70 mV and about 70 mV, as calculated using electrophoretic light scattering. In some embodiments, the zeta potential is less than or equal to zero mV. In some embodiments, the zeta potential is 0±5 mV. In some embodiments, the zeta potential is about −70, −65, −60, −55, −50, −45, −40, −35, −30, −25, −20, −15, −10, −5, −4, −3, −2, −1, 1, 2, 3, 4, 5, 10, 15, 20, 25, 30, 35, 40, 45, 50, 55, 60, 65, or 70 mV. Zeta potential can be adjusted using methods known in the art, such as by the addition of salts and/or by modifying the pH.

In one embodiment, the liposome constructs comprise an emulsifier or binding agent to enhance agglomeration. Exemplary emulsifiers include, without limitation, acacia, glyceryl monooleate, glyceryl monostearate, polyoxyethylene sorbitan monostearate, polyoxyethylene sorbitan monooleate, polyoxyethylene sorbitan monolaurate, sodium lauryl sulfate, sodium dioctyl sulfosuccinate, sorbitan oleate, sorbitan palmitate, sorbitan stearate, and triethanolamine oleate.

The SUVs/liposome constructs can comprise a surface modifying group and/or a surface antigen. In some embodiments, the surface modifying group is polyethylene glycol (PEG). The level of pegylation of the liposome surface may vary, for example, from 1 mol % to 20 mol %, or higher. In some embodiments, the surface antigen is rhodamine.

Stability of liposomes depends upon the various properties such as surface charge, size, surface hydration, and fluidity of lipid bilayers. Surface charge determines interaction of liposomes with ocular membrane. The liposomal membrane can have a positive charge, a negative charge, or no (neutral) charge. Likewise, the individual lipids that comprise the lamella of the SUVs can each have a net positive, a net negative, or a net neutral charge. Local regions of charge can influence the properties of SUVs, even where the net charge is neutral.

The liposome constructs can be responsive to stimuli, such as pH, temperature, light, oxidation, enzymatic degradation, radiation, or combinations thereof.

The liposome constructs of the embodiments of the present invention can contain at least about 0.05 mg, 0.1 mg, 0.2 mg, 0.3 mg, 0.4 mg, 0.5 mg, 0.6 mg, 0.7 mg, 0.8 mg, 0.9 mg, or 1 mg urea per µL of packed liposome construct pellet. Packed liposome construct pellets are prepared by ultracentrifuging a sample containing liposome constructs at about 90,000 g for about 5 minutes and decanting the supernatant.

The liposome constructs of the embodiments of the present invention are capable of extending dwell time of urea at the vitreoretinal interface, and can be optimized to release their cargo at the desired rate. For example, the liposome construct (e.g., a sustained-release drug delivery system) of the embodiments of the present invention can release urea for at least about 2, 4, 6, 12, 18, 24, 48, or 72 hours, or at least about 1, 2, 3, 4, 5, or 6 weeks after a single administration. In one embodiment, the liposome construct can release about 10% or less of the encapsulated urea at 4-8 hours after administration. In one embodiment, the liposome construct can release about 50% or less of the encapsulated urea at 8-12 hours after administration. In one embodiment, the liposome construct can release at least about 75% of the encapsulated urea at 1 hour after administration. In one embodiment, the liposome construct can release at least about 80% of the encapsulated urea at 8 hours after administration. In one embodiment, the liposome constructs can release at least about 80% of the encapsulated urea at 24 hours after administration. Release rates can be varied depending on the desired dosage by varying the formulation of the liposome constructs.

In some aspects, it might be desirable for a composition comprising liposome constructs to have a tiered-release profile. In these embodiments, it may be envisioned that some urea is released immediately after injection, while some urea is released at various time points after injection, e.g., every 6 hours, every 12 hours, every day, every two days, every three days, every week, every month, etc. Accordingly, the composition can comprise a mixed population of SUVs, wherein the SUVs have one or more different properties, such as size, charge, composition of the lipid bilayer(s), modification(s) of the lipid bilayer(s), or a combination thereof, thereby varying the release rate of the urea.

The liposome constructs can comprise an antibody or antigen-binding fragment thereof that specifically binds to an antigen expressed in cells of the retina or macula. In some embodiments, the cells are Müller cells, retinal ganglion cells, retinal axonal cells, inner limiting membrane cells, retinal pigment epithelial cells, or retinal astrocytes. In some embodiments, the antigen is expressed on the surface of the cells. In some embodiments, the antigen is specifically expressed on the surface of the Müller cells. In some embodiments, the antigen is selected from the group consisting of vimentin, glutamine synthetase, fibroblast growth factor receptor 1 (FGFR1), fibroblast growth factor receptor 4 (FGFR4), fibroblast growth factor receptor 9 (FGFR9), Heparin Binding Growth Factor, glial fibrillary acidic protein (GFAP), CD16, CD17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), and retinaldehyde binding protein. The antibody can be attached to the surface of the liposomes. In some embodiments, the antibody is attached to a PEG on the surface of the liposomes.

III. Preparation of Liposome Constructs

SUVs can be made by methods known in the art, such as solvent evaporation, reverse phase evaporation, dehydration-rehydration, detergent dialysis, thin film hydration (Bangham method), detergent depletion, solvent (e.g., ether/ethanol) injection, emulsion methods, dense gas methods, supercritical fluid methods, etc. For example, a lipid mixture can be dissolved in an organic solvent and then dried to form a lipid film. The dried lipid film can then be hydrated and sized, for example, by extruding them through orifices of decreasing pore size, which results in liposome constructs comprised of unilamellar liposomes, and having a standardized uniform diameter.

To prepare liposome constructs comprising urea, the lipid film can be hydrated with a solution of urea, such that it becomes encapsulated within the interior of the SUVs that form liposome constructs. After removal of the unentrapped urea using column chromatography or dialysis, the liposomes can be sized as described above. Preferably, the urea is in a saturated solution or a supersaturated solution.

An alternative method of preparing liposome constructs comprising urea is to load the urea into pre-formed SUVs using a pH gradient method where the aqueous interior of the liposome has a lower pH than the external medium surrounding the liposome construct. Urea will migrate and concentrate within the liposome construct. Another method of loading urea into the interior of liposome constructs employs an ammonium sulfate gradient method.

There are many different methods of loading active agents into liposome constructs that are known in the art and are within the scope of this invention.

IV. Compositions Comprising Liposome Constructs and Methods of Use

In the past, it has been very difficult to administer active agents to the surface of the retina because they disperse in the vitreous body immediately after delivery, and sufficient concentrations do not reach the back of the eye. Water soluble drugs, such as urea, pose a particular challenge in this regard. The pharmaceutical compositions of the invention solve this problem because of their physical characteristics. In particular, the SUVs are small enough that they can be sterile-filtered, but can still entrap a therapeutically effective amount of urea. They agglomerate sufficiently upon injection such that they stay together in a liposome construct once administered, rather than dispersing throughout the vitreal fluid, and they are denser than the vitreous, such that they can settle onto and blanket the retinal surface. While "empty" SUVs (i.e., without encapsulated urea) will agglomerate following intravitreal injection, they disperse readily under gentle agitation of the vitreous humor. However, the same SUVs with encapsulated urea form a liposome construct that agglomerates following intravitreal injection and does not disperse under gentle agitation of the vitreous humor. Multiple different urea-containing liposome constructs of the invention demonstrate agglomeration that withstands gentle agitation of the vitreous humor, which allows the drug to be released from an agglomerated depot spatially within the vitreous, rather than from a dispersed position throughout the vitreous. Thus, the pharmaceutical compositions of the invention provide novel formulations for effectively delivering active agents to the vitreoretinal interface.

The liposome constructs of the invention form an agglomeration of SUVs, which agglomeration is stabilized by the encapsulation of urea within the SUVs. The density of the composition causes it to sink in the vitreal fluid, which is optionally facilitated by delivery to a subject in a supine position, resulting in targeted delivery to, and release of urea at, the retinal interface, rather than in the whole eye. Therefore, the disclosure provides a method of increasing the exposure of the retina of a subject to urea, where the method includes administering the liposome construct comprising urea to the eye of the subject.

In certain aspects, this disclosure provides compositions comprising liposome constructs as described above, optionally further comprising one or more carriers, diluents, excipients, or other additives. The compositions can be at a pH of about 5.0 to about 8.5.; preferably, the pH is about 5.0, 5.5, 6.0, 6.5, 7.0, 7.5, 8.0, or 8.5. Such compositions can include liposome constructs comprising urea.

In addition to being encapsulated in the SUVs, urea can also be present in the carrier or buffer comprising the liposome constructs. The concentration of unencapsulated urea in the carrier or buffer can vary depending upon the desired characteristics of the composition. For example, the composition can be formulated to maintain equilibrium between the concentration of encapsulated urea and unencapsulated urea, so that the concentration of urea that is encapsulated remains stable. In addition, the concentration of unencapsulated urea in the storage carrier or buffer can be different from its concentration in the composition that is administered. For example, the carrier or buffer can comprise a higher concentration of unencapsulated urea if an initial bolus dose is desired upon administration.

The composition can be in a variety of forms, such as solution, microparticle, nanoparticle, hydrogel, etc., or a combination thereof. In some embodiments, the liposome constructs are dispersed in a gel. In a preferred embodiment, the liposome constructs are in the form of an emulsion or a suspension.

As discussed herein, urea encapsulated in a liposome construct can be administered in a therapeutically effective amount for the in vivo treatment of diseases or disorders of the retina, particularly diabetic retinopathy. In this regard, it will be appreciated that the disclosed liposome constructs can be formulated so as to facilitate administration and promote stability of the urea. Thus, the liposome constructs of the embodiments of the present invention can be administered in a pharmaceutical composition.

Pharmaceutical compositions in accordance with the present invention can comprise a pharmaceutically acceptable, non-toxic, sterile carrier such as physiological saline, non-toxic buffers, preservatives and the like. For the purposes of the instant application, a "therapeutically effective amount" of urea means an amount sufficient to achieve a benefit, e.g., to induce PVD.

Usually, a suitable pharmaceutical composition can comprise one or more buffers (e.g. acetate, phosphate, citrate), surfactants (e.g. polysorbate), stabilizing agents (e.g. human albumin), and/or salts (e.g., acid addition salts, base addition salts) etc. The form and character of the pharmaceutically acceptable carrier or diluent can be dictated by the amount of active ingredient with which it is to be combined and other well-known variables. Examples of suitable aqueous and non-aqueous carriers that can be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of a certain particle size in the case of dispersions, and by the use of surfactants.

These compositions can also contain adjuvants such as preservatives, wetting agents, emulsifying agents and dispersing agents. Prevention of presence of microorganisms can be ensured both by sterilization procedures and by the inclusion of various antibacterial and antifungal agents, for example, paraben, chlorobutanol, phenol sorbic acid, and the like. Isotonic agents, such as sugars, sodium chloride, and the like, can also be added into the compositions. In addition, prolonged absorption of the injectable pharmaceutical form can be brought about by the inclusion of agents which delay absorption, such as aluminum monostearate and gelatin.

A pharmaceutical composition provided herein can also include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Accordingly, this disclosure provides a method of treating a disease or disorder of the eye, e.g., diabetic retinopathy, wherein the method comprises administering to a subject in need thereof a pharmaceutical composition comprising a liposome construct encapsulating urea, as provided herein, wherein a sufficient amount of the urea reaches and remains in contact with the retina for a period of time sufficient to treat the disease and/or to reach a desired endpoint, such as inducing PVD. To that end, the methods of the embodiments of the invention can further comprise positioning the subject in a supine position, i.e., on his or her back, to facilitate migration of the liposome construct composition to the posterior portion of the eye. Because the liposome constructs are denser than the vitreous, positioning a subject in this manner takes advantage of gravity and causes the liposome constructs to "sink" to the retina, which is located at the back of the eye, thereby achieving targeted delivery to the retina.

The herein provided liposome constructs are useful for the treatment or prevention of any disease or disorder that can be addressed by the delivery of urea to the retina, including the macula. Examples of diseases or disorders that can be treated or prevented using the liposome constructs and methods of the embodiments of the invention include one or more of age-related macular degeneration (AMD), branch or central retinal vein occlusion, central serous chorioretinopathy, choroidal detachment, congenital X-linked reinoschisis, diabetic macular edema (DME), diabetic retinopathy (DR), epiretinal membranes, familial exudative vitreoretinopathy, infectious retinitis, macular edema, macular hole, macular pucker, persistent fetal vasculature, presumed ocular histoplasmosis syndrome, retained lens fragment, retinoblastoma, retinal tears or detachment, retinitis pigmentosa, retinopathy of prematurity, river blindness (onchocerciasis), vitreomacular adhesion (VMA), vitreomacular traction syndrome, and wet macular degeneration. In some instances, it might be desirable to induce a condition in the eye, for example, PVD. Numerous disease states can be prevented or improved by inducing PVD, which can protect the retina from pathological angiogenesis.

Clinical response to administration of a liposome construct can be assessed using standard screening techniques, for example, optical coherence tomography (OCT), fundus photography, or fluorescein angiography. Clinical response can also be assessed by improvement in the symptoms associated with the disease or disorder. In some embodiments, the targeting of liposome constructs can be analyzed by observing fluorescent markers on or in the liposome constructs.

Methods of administering liposome constructs or compositions comprising liposome constructs to the vitreous of a subject are well-known to or can be readily determined by those skilled in the art. For example, administration can be via intravitreal injection, intravitreal implantation, iontophoresis, or a microelectromechanical device. Preferably, administration is via intravitreal injection, such as, for example, via an 18-31 gauge needle. In some instances, administration is via a 27-gauge needle or a 30-gauge needle. The volume that is typically delivered via vitreal injection is between about 50 µL and about 150 µL, preferably about 100 µL.

The concentration of liposome constructs of the embodiments of the invention that can be combined with carrier materials to produce a dosage form will vary depending upon many different factors, including the encapsulation efficiency of urea, whether treatment is prophylactic or therapeutic, other medications administered, and whether the patient is human or an animal. The amount of liposome construct to be administered is readily determined by one of ordinary skill in the art without undue experimentation, given this disclosure. Treatment dosages can be titrated using routine methods known to those of skill in the art to optimize safety and efficacy.

The composition comprising liposome constructs can be administered as a single dose or multiple doses. The composition can be administered as many times as needed to achieve a targeted endpoint, such as PVD induction. Injection intervals may vary. For example, the composition can be administered every 6, 12, 24, 48, or 72 hours, every 1, 2, 3, or 4 weeks, or every 1, 2, 3, 4, 5, 6, 9, 12, 18, 24, 36, or 48 months. Dosage regimens can be adjusted to provide the optimum desired response (e.g., a therapeutic or prophylactic response).

Pharmaceutical compositions can also be administered in combination therapy and/or combined with other agents.

This disclosure provides for the use of a pharmaceutical composition comprising a liposome construct encapsulating urea, as described herein, to treat or prevent diseases or disorders of the retina or macula. This disclosure also provides for the use of liposome constructs comprising urea as described herein in the manufacture of a medicament for treating or preventing diseases or disorders of the retina or macula. The disclosure further encompasses the use of a pharmaceutical composition comprising a liposome construct comprising urea for prevention, management, treatment, or amelioration of one or more symptoms associated with disease, disorder, or injury of the eye, either alone or in combination with other therapies.

VII. Kits

Also within the scope of the disclosure are kits comprising liposome constructs and/or compositions as provided herein and instructions for use. The kit can further contain at least one additional reagent, or one or more additional liposome constructs. Kits typically include a label indicating the intended use of the contents of the kit. The term "label" includes any writing, or recorded material supplied on or with the kit, or which otherwise accompanies the kit.

This disclosure further provides kits that comprise one or more liposome constructs, which can be used to perform the methods described herein. In certain embodiments, a kit comprises at least one type of liposome construct of the invention in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed liposome constructs can be readily incorporated into one of the established kit formats which are well known in the art.

All of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

EXAMPLES

Embodiments of the present invention can be further defined by reference to the following non-limiting examples, which describe in detail preparation of certain liposome constructs of the present invention and methods for using liposome constructs of the present invention. It will be apparent to those skilled in the art that many modifications, both to materials and methods, can be practiced without departing from the scope of the present disclosure.

Example 1

Study of Candidate Formulations

We initially considered several liposome formulations, shown in Table 1.

TABLE 1

| No. | Formulation Description | Formulation Rationale |
|---|---|---|
| 1 | 58 mol % DPPC<br>42 mol % cholesterol | Original formulation<br>DPPC: saturated<br>High cholesterol affects liposome stability in vitreal fluid |
| 2 | 58 mol % DOPC<br>42 mol % cholesterol | Substitute saturated DPPC with unsaturated DOPC (two chains) to evaluate a more "leaky" liposome |
| 3 | 58 mol % POPC<br>42 mol % cholesterol | Substitute DPPC with more biosimilar POPC (one unsaturated chain and one saturated chain) |
| 4 | 53 mol % DPPC<br>42 mol % cholesterol<br>5 mol % DPPE-PEG2000 | Replace 5 mol % DPPC with DPPE-PEG2000 to assess whether a PEG coating affects stability |
| 5 | 29 mol % DPPC<br>42 mol % cholesterol<br>29 mol % DPPG | Replace half of the DPPC with DPPG to evaluate the effect<br>of an overall negative charge on the liposomes |
| 6 | 80 mol % POPC<br>20 mol % DOTAP | Use POPC/DOTAP to evaluate the effect of an overall positive charge on the liposomes |
| 7 | 85 mol % DPPC<br>10 mol % DMPC<br>5 mol % DPPE-PEG2000 | Evaluate a heat sensitive formulation that releases liposome content more readily at slightly elevated temperatures (~40° C.) |
| 8 | 100% DPPC | Remove cholesterol for a simpler formulation |
| 9 | 100% DOPC | Remove cholesterol for a simpler "leaky" formulation |
| 10 | 100% DMPC | Remove cholesterol for a simpler formulation with a lower<br>transition temperature than DPPC |
| 11 | 100% POPC | Remove cholesterol for a simpler formulation with a biosimilar lipid |
| 12 | 91 mol % DPPC<br>9 mol % cholesterol | Reduce the amount of cholesterol to evaluate the effect on liposome stability in vitreal fluid |
| 13 | 67 mol % DMPC<br>33 mol % DMPG | Evaluate a "saturated" liposome that is still fluid enough at<br>room temp. without use of cholesterol |
| 14 | 33% DPPC<br>13% DSPC<br>32% DOPC<br>17% 18:2 PC<br>5% 20:4 PC | Evaluate an egg PC-like formulation that mimics the fatty acid composition found in egg PC |
| 15 | 80% PC<br>20% cholesterol | Evaluate a shorter and less complex lipid, particular formulation as a control. |

All lipids were obtained from Avanti Polar Lipids, Inc. (Alabaster, Ala.). Formulations 1, 3, 8, 11, and 12 were prepared with carboxyfluorescein. Briefly, a 100 mM carboxyfluorescein solution was prepared in 1× PBS (HyClone™ Cat. No. SH0256, GE Healthcare, Marlborough, Mass.), and the pH was adjusted to 6.5-7.5 with 1% NaOH. This solution was filtered and used to prepare self-quenching liposomes. Lipid films were dried under a stream of nitrogen, followed by vacuum for a minimum of 2 hours, and were rehydrated with the 100 mM carboxyfluorescein solution. The rehydrated liposomes were extruded through a 0.2 µm filter membrane (Millex®, MilliporeSigma, Darmstadt, Germany). The liposomes were separated from the unencapsulated carboxyfluorescein by size-exclusion chromatography on a Sephadex G75 column (Sigma Aldrich, St. Louis, Mo.).

Each formulation was tested for liposome stability and carboxyfluorescein leakage rate in PBS, HBSS, and rabbit vitreous humor over 24 hours. To determine the time-course of carboxyfluorescein leakage from the liposomes mixed in either PBS, HBSS (HyClone™ Cat. No. SH30256, GE Healthcare, Marlborough, Mass.) or rabbit vitreous humor (BTS Research, San Diego, Calif. or Absorption Systems LP, Exton, Pa.), triplicate 80 µL aliquots of either PBS or HBSS were added to ELISA strips (Cat. No. 446473, Thermo Scientific, Waltham, Mass.) with an automatic pipetter; triplicate 100 µL aliquots of vitreous humor were added with a sterile 1 mL pipette. Twenty µL of liposome formulations were added on top of each fluid in triplicate. Ten µL of RIPA buffer (Cat. No. 89901, Thermo Scientific, Waltham, Mass.) was added in triplicate to identical samples to determine the maximum fluorescence emission in PBS, HBSS, and vitreous humor. Negative controls with either 100 µL PBS, 80 µL HBSS+20 µL PBS, or 100 µL vitreous humor +20 µL PBS were included. The plate was sealed with a self-adhesive plastic film and shaken vigorously for 3 cycles in a VMax Kinetic Microplate Reader (Molecular Devices, Sunnyvale, Calif.) before fluorescence emission was determined. The gain was set at 800, as determined from the gain required to produce 50% maximum emission in a well containing liposomes with PBS and RIPA buffer at Time 0.

The samples were incubated at 37° C. for 2 hours; emission was read every minute. The samples were then read every 15 minutes for another 22-24 hours. Liposomes were lysed with RIPA buffer and tested over 24 hours for maximum fluorescence emission in PBS, HBSS, and rabbit vitreous humor. All tested liposome formulations were stable over the course of 24 hours. The lysed liposome samples had increased fluorescence emission over 24 hours, demonstrating that the intact liposomes had successfully encapsulated carboxyfluorescein (FIG. 1A-1E).

Example 2

Urea Encapsulation and Stability Studies

Urea has been shown to induce posterior vitreous detachment (PVD) in patients with moderate to severe diabetic retinopathy; however, clinical applications have been hampered by the inability to deliver enough drug to the back of the eye for a sustained period.

Formulations 1, 2, 3, 12, and 14 (Table 1) were prepared. All lipids except cholesterol were obtained in chloroform solution; cholesterol powder was added to the chloroform solution in the desired ratio. Cholesterol was evaporated via a nitrogen stream, followed by freeze-dry evaporation of chloroform-lipid samples. The resulting lipid cake was hydrated with 100 µL of 1 g/mL urea (Invitrogen Cat. No. 15505035, Carlsbad, Calif.) solution, agitated for 30 min. at 4° C., and extruded using a two-step extrusion process with 0.8 µm and 0.2 µm filters. In order to find the encapsulation efficiency, an aliquot of the 1 g/mL urea solution was obtained and the mass of urea in the loading buffer was measured. Following extrusion, liposomes were pelleted in an ultracentrifuge (Airfuge®, Beckman Coulter, Indianapolis, Ind.) at 90,000 g for 5 minutes at room temperature, and the buffer was decanted. Pellets were re-suspended in 100 µL of deionized water and used for further experiments and/or analysis.

The re-suspended sample volume, after washing with 100 µL of PBS, was measured and used to determine the liposome pellet volume, shown in Table 2.

TABLE 2

| No. | Formulation | Re-suspended Sample Vol. (µL) | Wet Pellet Vol. (µL) |
|---|---|---|---|
| 1 | 58 mol % DPPC 42 mol % cholesterol | 122 | 22 |
| 2 | 58 mol % DOPC 42 mol % cholesterol | 121 | 21 |
| 3 | 58 mol % POPC 42 mol % cholesterol | 126 | 26 |
| 12 | 91 mol % DPPC 9 mol % cholesterol | 112 | 12 |
| 14 | 33% DPPC 13% DSPC 32% DOPC 17% 18:2 PC 5% 20:4 PC | 115 | 15 |

The amount of encapsulated urea and the urea loading (encapsulation) efficiency was determined for each formulation. Following 0.2 µm filter extrusion, liposome samples were ultra-centrifuged (Airfuge®, Beckman Coulter, Indianapolis, Ind.) at 90,000 g for 5 minutes at room temperature to separate free urea in solution from the encapsulated urea in the packed liposome pellet. The supernatant was decanted. The upper limit for encapsulation efficiency was found by measuring the amount of urea encapsulated within the packed pellet mass (re-suspended in 100 µL DI $H_2O$) and dividing by the mass of urea in the loading buffer. Each pellet was washed re-suspending 1× PBS (MP Biomedicals, Santa Ana, Calif.), followed by ultra-centrifugation at 90,000 g for 5 minutes to eliminate the fraction of urea associated with the outside of the liposome constructs. The supernatant was removed and the pellet was suspended in 100 µL deionized water and boiled for 5 seconds, followed by two freeze-thaw cycles to destabilize lipsome constructs. Pellet data were generated in triplicate using three 1 µL samples. Supernatant data were generating in triplicate using three 1 µL samples. The ratio of encapsulated urea (pellet) to urea in the initial loading buffer was established using a urea assay kit (Abnova Corp. Cat. No. KA1652, Taipei City, Taiwan). The packed pellet was washed a second time with 100 µL of PBS in order to remove any urea associated with the liposome particles but not truly encapsulated. The amount of urea encapsulated within the washed packed pellet mass (re-suspended in 100 µL DI $H_2O$) divided by the mass of urea in the loading buffer provides the lower limit of the encapsulation efficiency. We achieved encapsulation efficiencies of at least X and less than Y during the loading process.

The lower limits of loading efficiency and total mass of encapsulated urea are shown in Table 3. The upper limits of loading efficiency and total mass of encapsulated urea are shown in Table 4.

TABLE 3

| No. | Formulation | Encapsulation Efficiency (%) | Encapsulated Urea (total mg in 100 µL) |
|---|---|---|---|
| 1 | 58 mol % DPPC 42 mol % cholesterol | 11.7 | 10.6 |
| 2 | 58 mol % DOPC 42 mol % cholesterol | 9.9 | 8.5 |
| 3 | 58 mol % POPC 42 mol % cholesterol | 13.6 | 12.5 |
| 12 | 91 mol % DPPC 9 mol % cholesterol | 6.9 | 5.5 |
| 14 | 33% DPPC 13% DSPC 32% DOPC 17% 18:2 PC 5% 20:4 PC | 6.1 | 4.7 |

TABLE 4

| No. | Formulation | Encapsulation Efficiency (%) | Encapsulated Urea (total mg in 100 µL) |
|---|---|---|---|
| 1 | 58 mol % DPPC 42 mol % cholesterol | 31.8 | 30.6 |
| 2 | 58 mol % DOPC 42 mol % cholesterol | 24.3 | 24.0 |
| 3 | 58 mol % POPC 42 mol % cholesterol | 34.1 | 32.4 |
| 12 | 91 mol % DPPC 9 mol % cholesterol | 16.9 | 17.1 |
| 14 | 33% DPPC 13% DSPC 32% DOPC 17% 18:2 PC 5% 20:4 PC | 19.5 | 19.2 |

Twenty-four hour stability testing of the liposomes in 1× PBS and in rabbit vitreous humor (Absorption Systems LP, Exton, Pa.) was carried out at room temperature for all five formulations (Formulations 1, 2, 3, 12 and 14). Liposome formulations were prepared as described above. For stability testing in 1× PBS, 100 μL of 1× PBS was added to the wet liposome pellet volume, as provided in Table 2. The volume of liposome sample (100 μL) for the stability tests was approximately 1:1 in vitreous humor. Samples were kept at room temperature.

The concentration of free and encapsulated urea was measured as described above at 6, 12, and 24 hours post encapsulation. Encapsulated urea was reported at each time point and plotted to show the release profile of urea (FIG. 2A-2D). Formulation 2 (58 mol % DOPC, 42 mol % cholesterol) showed the best urea release characteristics over 24 hours in both 1× PBS and vitreous humor, having released approximately 25% of encapsulated urea at 24 hours.

Example 3

Characterization and Optimization of Formulation 2 (58 mol % DOPC, 42 mol % cholesterol) Liposome Constructs Particle Size Analysis Particle size analysis was performed using a Microtrac (Montgomeryville, Pa.) 150 instrument and Microtrac Particle Size Analyzer software, version 10.1.3. Particle size analysis of Formulation 2 without urea showed that 90% of liposome constructs were under 250 nm, and that 10% were under 100 nm. Thus, the liposome construct particle size of Formulation 2 without urea ranged from about 100 nm to about 250 nm. Particle size analysis of Formulation 2 with encapsulated urea showed that 90% of liposome constructs were under 300 nm and that 10% were under 90 nm. Thus, the liposome construct particle size of Formulation 2 with encapsulated urea ranged from about 90 nm to about 300 nm.

Optimization of Buffer Formulation

Optimal buffer compositions were assessed for encapsulation efficiency and stability of the liposome constructs at 4° C. for 96 hours. Formulation 2 liposome constructs with encapsulated urea were made with 6 different buffer compositions, shown in Table 5.

TABLE 5

| Buffer No. | Buffer Formulation |
| --- | --- |
| 1 | 0.95 g/mL urea in diH2O |
| 2 | 0.95 g/mL urea in 0.5x PBS |
| 3 | 0.95 g/mL urea in 1x PBS |
| 4 | 0.95 g/mL urea in 2x PBS |
| 5 | 0.95 g/mL urea + citric acid (pH 6.5) |
| 6 | 0.95 g/mL urea + citric acid (pH 6.5) + 10% sucrose |

Each buffer formulation is an aqueous hydration medium that was added to dry lipid cake (Formulation 2), followed by extrusion, as described above. The loading efficiency and total mass of encapsulated urea are shown in Table 6.

TABLE 6

| Buffer No. | Encapsulation Efficiency (%) | Encapsulated Urea (total mg in 100 μL) |
| --- | --- | --- |
| 1 | 21.4 | 21 |
| 2 | 21.0 | 20 |
| 3 | 20.6 | 20 |
| 4 | 18.3 | 18 |

TABLE 6-continued

| Buffer No. | Encapsulation Efficiency (%) | Encapsulated Urea (total mg in 100 μL) |
| --- | --- | --- |
| 5 | 19.5 | 19 |
| 6 | 18.7 | 18 |

The buffer composition of deionized water and urea had the highest urea encapsulation efficiency; 0.5× PBS and 1× PBS buffers with urea were the next best. However, stability of liposome constructs in the buffer containing citric acid (pH 6.5), 10% sucrose, and 0.95 g/mL urea did not demonstrate a change in encapsulated urea after 96 hours. The 2× PBS urea buffer showed the least stability, with an encapsulated urea concentration loss of roughly 30%.

Syringe Stability Test

Formulation 2 liposome constructs were used to evaluate liposome construct behavior with higher volume-to-volume concentrations of liposome constructs. To test the effect of aspirating liposome constructs through a syringe, pellets were prepared as described above, two pellets were combined, re-suspended to a total volume of 100 μL 0.5× PBS, and aspirated through a 27-gauge or 30-gauge needle. The amounts of encapsulated and free urea were determined as described above, and are shown in Table 7.

TABLE 7

| Treatment | Encapsulation Efficiency (%) | Encapsulated Urea (total mg in 100 μL) |
| --- | --- | --- |
| 27-gauge needle | 17.5 | 35 |
| 30-gauge needle | 17.5 | 36 |
| Negative control (no treatment) | 17.5 | 35 |

Combining two pellets increased that amount of encapsulated urea, but not the encapsulation efficiency. No loss of liposome construct integrity was observed with either the 27-gauge or 30-gauge needle. However, when 3 pellets were combined in 100 μL total volume, sample loss was roughly 40% when aspirated and dispensed from a 27-gauge needle.

Temperature Stability Test

Figure 3:
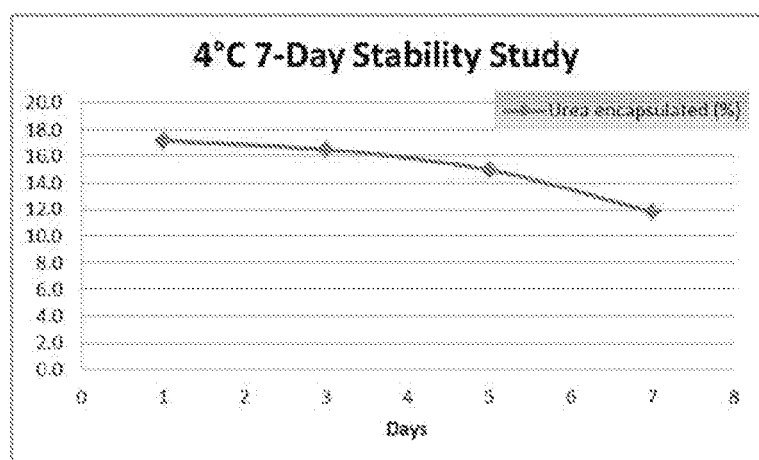
FIG. 3A-3C show stability over a 7-day period of urea-encapsulated liposome constructs made from Formulation 2 (described in Table 1) and stored at 4° C.
Figure 3:
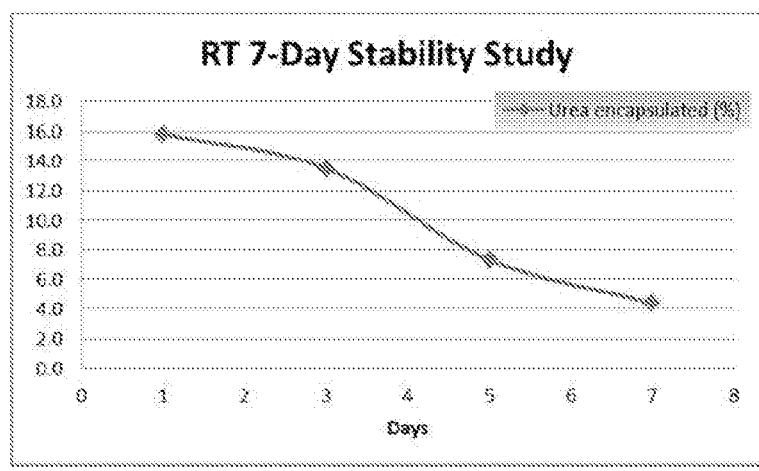
Figure 3:
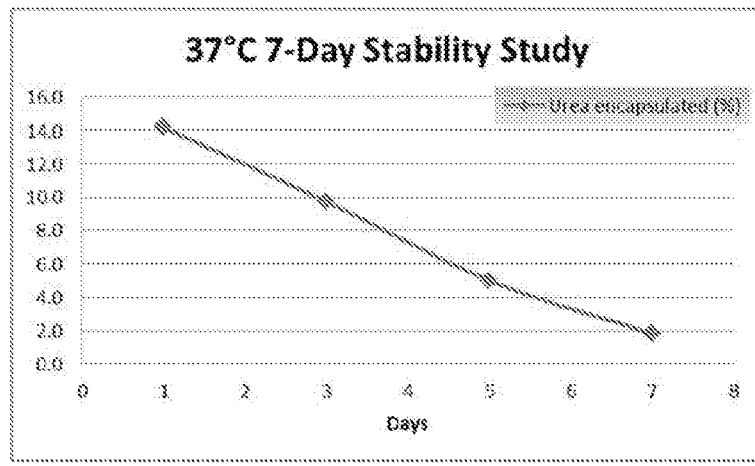

A 7-day temperature-controlled stability test in 0.5× PBS at 4° C., room temperature, and 37° C. was performed for Formulation 2 urea encapsulated liposome constructs, prepared and analyzed as described above. Results are shown in Table 8 and in FIG. 3A-3C, where total encapsulated urea (mg) in a 100 μL sample was measured.

TABLE 8

| Formulation 2 2x Pellets, 0.5x PBS | 4° C. Encapsulated Urea (mg) | Room Temperature Encapsulated Urea (mg) | 37° C. Encapsulated Urea (mg) |
| --- | --- | --- | --- |
| 0 days | 35 | 36 | 35 |
| 1 day | 35 | 32 | 28 |
| 3 days | 33 | 27 | 19 |
| 5 days | 30 | 14 | 9 |
| 7 days | 23 | 7 | 2 |
| Half-life | Not reached | ~4.75 days | ~4 days |

Example 4

Preparation and Further Characterization of Urea-Encapsulated Liposome Construct Formulations Using 1,2-Dioleoyl-sn-glycero-3-phosphocholine (DOPC) and cholesterol, liposomes were formed in the presence of urea to create urea-encapsulated liposome constructs. Materials used are summarized in Table 9.

TABLE 9

| Compound | Grade | Manufacturer | Lot |
|---|---|---|---|
| Urea | USP | EMD | K46524030524 |
| DOPC | NA | Avanti Polar Lipids | 181PC-318 |
| Cholesterol | NA | Avanti Polar Lipids | CH-102 |
| Ethanol | USP | Spectrum | 15120345 |
| PBS | NA | Hyclone Lab | 169611 |

Figure 4:
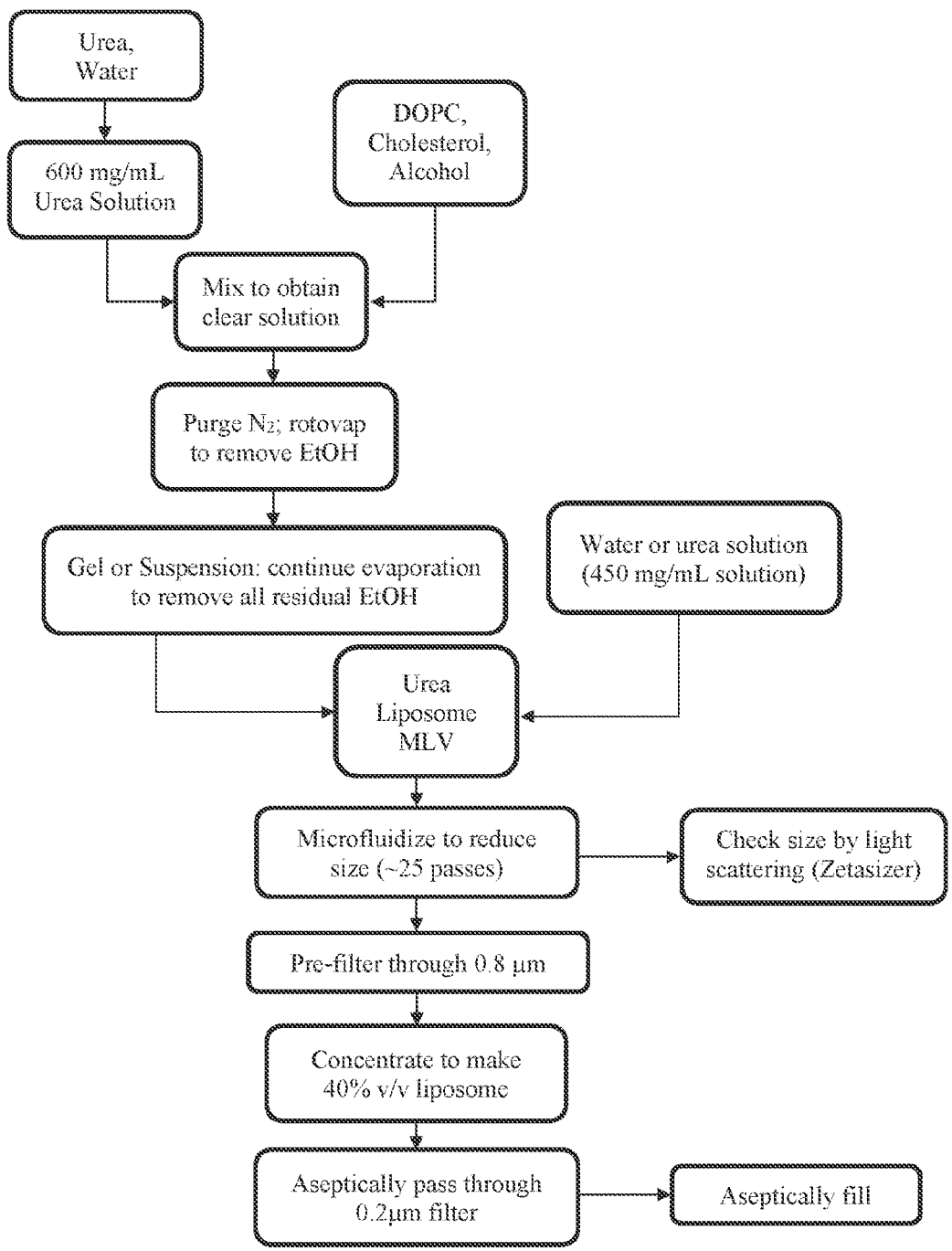
FIG. 4 shows a flow chart of a reverse-phase evaporation method for production of liposome constructs comprising encapsulated urea.

Reverse-phase evaporation, followed by micro fluidization (Model M110 EH, Microfluidics Corp., Westwood, Mass.), were performed to prepare urea-encapsulated liposome constructs with a particle size under 200 nm. Several batches were made in order to optimize the process steps and a small batch, F4B, was the first batch made per the optimized method (FIG. 4) and characterized. A standard series of tests, described below, was used to characterize subsequent batches.

The volume of aqueous portion of a 100 µL sample was separated from the pellet volume via centrifugal filtration, measured, and the pellet volume calculated. The total urea and the free urea concentrations were measured by high-performance liquid chromatography (HPLC) and used to calculate the encapsulated urea concentration and encapsulation efficiency (degree of urea incorporation). Zeta potential and particle size and distribution were measured by laser light scattering (LLS) using a Zetasizer (Malvern Instruments Ltd., Worcestershire, UK). Injectability through a 30G needle was confirmed by testing the total and free urea concentrations again, and calculating the encapsulated urea concentration. The volume lost during filtration through a 0.2 µm filter was ascertained by measuring the volume of a sample before and after filtration. The specific gravity of the batch was measured gravimetrically for a known volume, and agglomeration in vitreous humor or PBS was visually evaluated. Finally, the in vitro release of encapsulated urea was measured using a 20 kDa dialysis cassette at 37° C., over 7 days, with a sample volume:buffer volume ratio of 100 µL:5 mL. The total urea concentration was measured by HPLC, and the amount of encapsulated urea released was calculated based on the initial free urea concentration and the total urea concentration at each respective time point.

The composition of Batches F5 and F5B was 58 mol % DOPC and 42 mol % cholesterol; the batch size was 17 grams (1500-1600 doses). A 600 mg/mL saturated urea solution was used to make urea-encapsulated liposome constructs. After micro-fluidization, the batch was homogenized further to reduce the particle size of the liposomes to an acceptable size. After 0.8 µm filtration, the batch was aliquoted into two volumes, which were separately concentrated to a 40% liposome:60% saturated urea buffer (vol/vol ratio), using a stir cell device (Amicon, 50 mL, max pressure 75 psi) with a 10 kDa cut-off ultrafiltration membrane (MilliporeSigma, Darmstadt, Germany, Cat. No. PLGC04310), and sterile filtered. The final volume of batch F5 was 105 mL, and the final volume of batch F5B was 51 mL. Batches F11-F13 also had a composition of 58 mol % DOPC and 42 mol % cholesterol.

The composition of Batch F6 was 91 mol % DOPC and 9 mol % cholesterol; the batch size was 3 grams (1500-1600 doses). A 450 mg/mL saturated urea solution was used to make urea-encapsulated liposome constructs. The batch was concentrated and sterile filtered as described for Batches F5 and F5B.

The composition of Batch F8 was 70 mol % DOPC and 30 mol % cholesterol; the batch size was 3 grams (1500-1600 doses). A 450 mg/mL saturated urea solution was used to make urea encapsulated liposome constructs. The batch was concentrated and sterile filtered as described for Batches F5 and F5B.

The composition of Batch F9 was 45 mol % DOPC and 55 mol % cholesterol; the batch size was 3 grams (1500-1600 doses). A 450 mg/mL saturated urea solution was used to make urea-encapsulated liposome constructs. The batch was microfluidized for 20 minutes, with particle size of the batch measured every 3 minutes. After 20 minutes of microfluidization, the liposome particle size reached 1200 nm, well above the 200 nm target. Phase separation was observed when the sample volume was stored overnight after microfluidization. Homogenization of the batch was performed with the beadbeater for 5 minutes in order to successfully pass the sample through a 0.8 µm filter. The batch was concentrated and sterile filtered as described for Batches F5 and F5B. Sterile filtration through a 0.2 µm filter was very difficult, and at least ⅓ of the batch volume was lost during processing, due to complications from the high amount of large particles.

The composition of Batch F10 was 58 mol % DOPC and 42 mol % cholesterol, with approximately 6% (w/w) of the cholesterol having a fluorescent label. The batch was made by reverse phase evaporation, followed by microfluization, sonication, and filtration, as described above.

Figure 5:
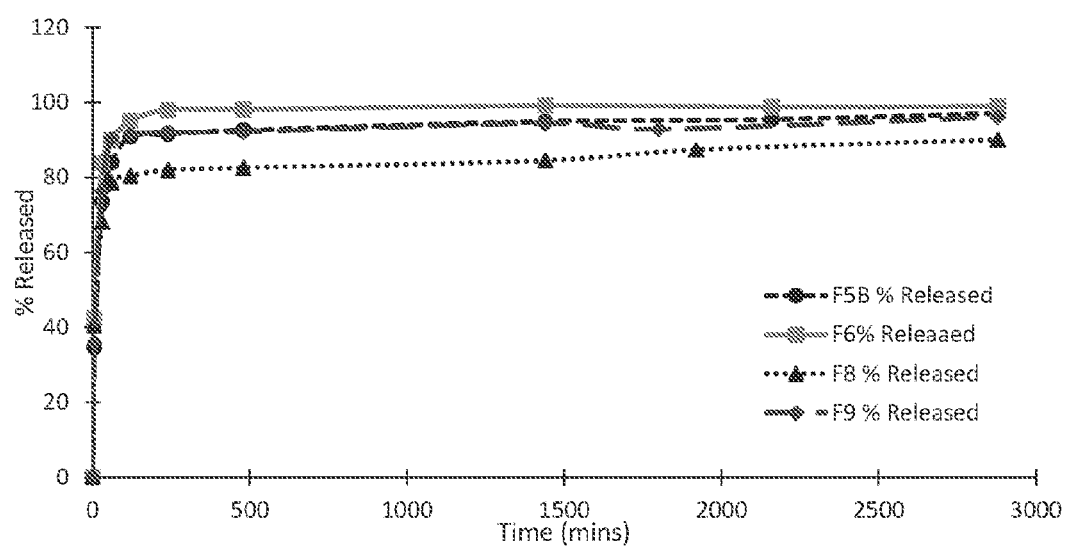
FIG. 5 shows in vitro urea release data for four batches of liposome constructs.

Results of characterization testing are shown in Table 10. Particle size and distribution are shown in Table 11. In vitro release data are shown in Table 12, Table 13, and FIG. 5.

TABLE 10

| Test | F5 Results | F5B Results | F6 Results | F8 Results | F9 Results |
|---|---|---|---|---|---|
| Saturated Urea Buffer Volume in 100 µL | 60 µL | 60 µL | 60 µL | 60 µL | 60 µL |
| Pellet Volume in 100 µL | 40 µL | 40 µL | 40 µL | 40 µL | 40 µL |
| Total Urea Conc. | 271.6 mg/mL | 331.9 mg/mL | 331.2 mg/mL | 266.7 mg/mL | 414.8 mg/mL |
| Free Urea Conc. | 292.1 mg/mL | 444.1 mg/mL | 313.3 mg/mL | 312.4 mg/mL | 442.3 mg/mL |
| Encapsulated Urea Conc. | 240.9 mg/mL | 391.88 mg/mL | 357.9 mg/mL | 256.7 mg/mL | 373.6 mg/mL |
| Encapsulation Efficiency (%) | 40.2% | 52.5% | 79.5% | 57.0% | 83.0% |
| Zeta Potential | −0.638 mV | −3.41 mV | −2.14 mV | −3.4 mV | −9.3 mV |
| Injectability through 30 G needle | No change in encapsulated urea conc. | No change in encapsulated urea conc. | No change in encapsulated urea conc. | No change in encapsulated urea conc. | No change in encapsulated urea conc. |

TABLE 10-continued

| Test | F5 Results | F5B Results | F6 Results | F8 Results | F9 Results |
|---|---|---|---|---|---|
| Volume loss after 0.2 μm filtration | None | None | None | None | None |
| Specific Gravity | 1.060 g/mL | 1.098 g/mL | 1.09 g/mL | 1.072 g/mL | 1.1147 g/mL |
| Agglomeration in PBS or Vitreous Humor | Agglomerated in vitreous | Agglomerated in vitreous | Agglomerated in PBS | Agglomerated in PBS, then dispersed instantly | Agglomerated in PBS |

TABLE 11

| Batch | Composition | Z Avg. Diameter (nm) | PdI |
|---|---|---|---|
| F5 | 58 mol % DOPC and 42 mol % cholesterol | 114.5 | 0.469 |
| F5B | 58 mol % DOPC and 42 mol % cholesterol | 112.567 | 0.367 |
| F10 | 58 mol % DOPC and 42 mol % cholesterol (fluorescently labeled) | 137.067 | 0.318 |
| F11 | 58 mol % DOPC and 42 mol % cholesterol | 107.3 | 0.205 |
| F12 | 58 mol % DOPC and 42 mol % cholesterol | 106.367 | 0.096 |
| F13 | 58 mol % DOPC and 42 mol % cholesterol | 110.8 | 0.093 |
| F6 | 91 mol % DOPC and 9 mol % cholesterol | 58.343 | 0.637 |
| F8 | 70 mol % DOPC and 30 mol % cholesterol | 120.3 | 0.213 |
| F9 | 45 mol % DOPC and 55 mol % cholesterol | 161.867 | 0.681 |

TABLE 12

| Time | F5 % Rel. | F5B Urea (mg) | F5B % Rel. | F6 Urea (mg) | F6 % Rel. | F8 Urea (mg) | F8 % Rel. | F9 Urea (mg) | F9 % Rel. |
|---|---|---|---|---|---|---|---|---|---|
| 0 | 0.0 | 0.0 | 0.0 | 0.0 | 0.0 | 0.0 | 0.0 | 0.0 | 0.0 |
| 5 min | 29.9 | 49.3 | 34.6 | 45.3 | 42.5 | 0.0 | 40.6 | 0.0 | 36.0 |
| 30 min | 71.6 | 104.7 | 73.5 | 86.4 | 83.8 | 83.2 | 68.1 | 106.6 | 76.4 |
| 60 min | 85.0 | 119.5 | 83.9 | 97.4 | 89.9 | 95.4 | 78.7 | 125.2 | 90.3 |
| 2 hours | 88.8 | 129.4 | 90.9 | 101.5 | 95.1 | 98.6 | 80.4 | 128.7 | 91.5 |
| 4 hours | 89.6 | 130.5 | 91.6 | 103.3 | 98.0 | 100.6 | 82.0 | 130.6 | 92.1 |
| 8 hours | 90.2 | 131.9 | 92.6 | 105.0 | 98.1 | 101.7 | 82.6 | 133.6 | 92.2 |
| 12 hours | 90.4 | 132.5 | 93.0 | — | — | — | — | — | — |
| 24 hours | 90.4 | 135.2 | 94.9 | 106.6 | 99.2 | 104.6 | 84.5 | 135.6 | 94.5 |
| 36 hours | 92.9 | 136.0 | 95.5 | 106.6 | 98.8 | 106.7 | 87.4 | 134.5 | 92.9 |
| 48 hours | 95.1 | 138.3 | 97.1 | 105.5 | 99.0 | 107.4 | 90.1 | 136.6 | 96.1 |
| 120 hours | 99.3 | 140.6 | 98.7 | 102.8 | 97.5 | 114.7 | 96.8 | 140.3 | 99.0 |
| Total (Control) | NA | 142.4 | NA | 104.8 | NA | 121.0 | NA | 104.8 | NA |

TABLE 13

| Batch | Encapsulated Urea Half-Life (min.) |
|---|---|
| F5B | 41 |
| F6 | 28 |
| F8 | 95 |
| F9 | 45 |

Figure 6:
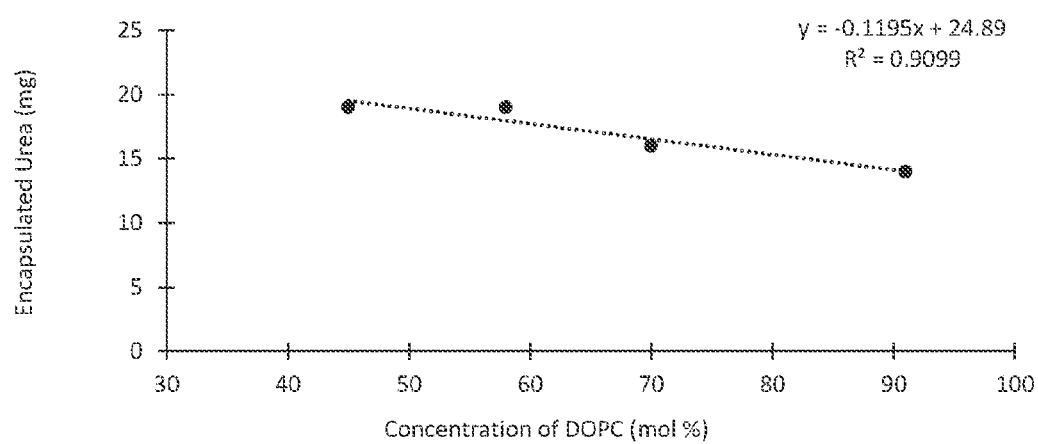
FIG. 6A-6B show the relationship between the amount of encapsulated urea in a 100 μL dose (40% liposome vol./60% urea buffer vol.) and the concentration of DOPC (FIG. 6A) or cholesterol (FIG. 6B).
Figure 6:
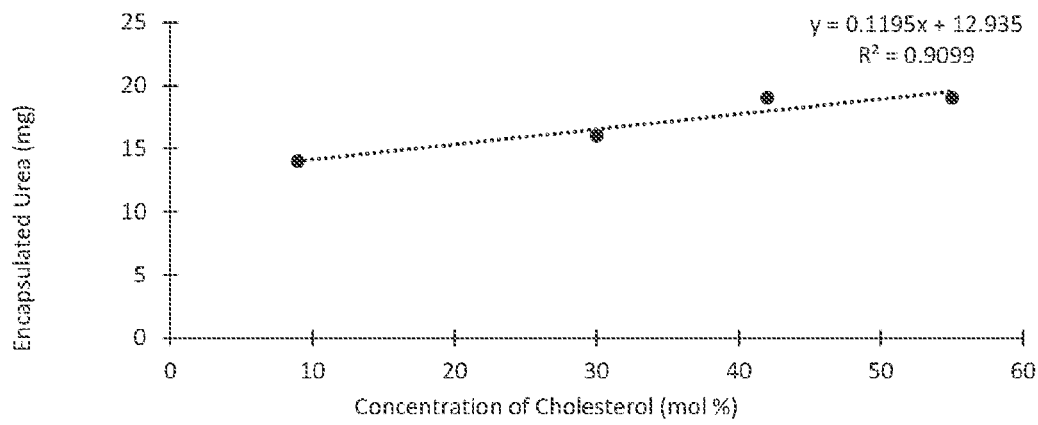

As the concentration of DOPC is increased in the formulation, the amount of urea encapsulated decreases (FIG. 6A). Conversely, as the concentration of cholesterol is increased in the formulation, the amount of urea encapsulated increases (FIG. 6B). The release rate of urea from the formulations is relatively similar and after 200 minutes, minimal amounts of urea are released at a steady rate. Based on the data collected, formulation F5/F5B with 58 mol DOPC and 42 mol % cholesterol has the targeted characteristics for an extended release urea formulation. The dwell time of urea in the eye when delivered in the liposome construct formulation is 8 times longer than that of neat urea.

Additional liposome construct batches were made by ethanol infusion, optionally with freeze/thaw cycling, and characterized as described above. Results are shown in Table 14 and Table 15.

TABLE 14

| Composition | Pellet % | Buffer % | Free Urea (mg/mL) | Total Urea (mg/mL) | Encapsulated Urea (mg/mL) | Encapsulation % |
|---|---|---|---|---|---|---|
| 58 mol % DOPC/42 mol % Cholesterol (with freeze/thaw) | 20 | 80 | 604.5 | 575.7 | 460.3 | 70.8 |
| 58 mol % POPC/42 mol % Cholesterol (with freeze/thaw) | 20 | 80 | 493.4 | 495.0 | 501.5 | 77.2 |
| 20 mol % DOTAP/80 mol % POPC (with freeze/thaw) | 13 | 87 | 433.6 | 422.1 | 344.9 | 53.1 |

TABLE 14-continued

| Composition | Pellet % | Buffer % | Free Urea (mg/mL) | Total Urea (mg/mL) | Encapsulated Urea (mg/mL) | Encapsulation % |
|---|---|---|---|---|---|---|
| 58 mol % DOPE/42 mol % Cholesterol (with freeze/thaw) | 20 | 80 | 476.9 | 473.9 | 461.9 | 71.1 |
| 58 mol % DOPE/42 mol % Cholesterol (without freeze/thaw) | 14 | 86 | 477.9 | 518.0 | 764.5 | 117.6 |
| Empty 58 mol % DOPC/42 mol % Cholesterol (with freeze/thaw) | 22 | 78 | 0.0 | 0.0 | 0.0 | 0.0 |
| Empty 58 mol % DOPC/42 mol % Cholesterol (without freeze/thaw) | 23 | 77 | 0.0 | 0.0 | 0.0 | 0.0 |
| Empty 58 mol % DOPC/42 mol % Cholesterol (with freeze/thaw) in 450 mg/mL Urea buffer | 12 | 88 | 254.5 | 247.0 | 192.0 | 42.7 |
| 29 mol % DPPC/29 mol % DPPG/42 mol % Cholesterol (with freeze/thaw) | 16 | 84 | 495.9 | 517.2 | 628.8 | 96.7 |

TABLE 15

| Composition | Z-Avg. Diam. (nm) | PdI | Avg. Zeta Pot. ± SD (mV) | Avg. Density ± SD (g/mL) | Agglomerates Upon Injection | Disperses Upon Gentle Agitation |
|---|---|---|---|---|---|---|
| 58 mol % DOPC/42 mol % Cholesterol (with freeze/thaw) | 168.6 | 0.094 | −2.71 ± 0.31 | 1.1363 ± 0.0068 | yes | no |
| 58 mol % POPC/42 mol % Cholesterol (with freeze/thaw) | 171.5 | 0.079 | −13.00 ± 0.44 | 1.1127 ± 0.0009 | yes | no |
| 20 mol % DOTAP/80 mol % POPC (with freeze/thaw) | 168.7 | 0.112 | 69.80 ± 1.22 | 1.1138 ± 0.0044 | yes | no |
| 58 mol % DOPE/42 mol % Cholesterol (with freeze/thaw) | 175.7 | 0.100 | −63.00 ± 1.77 | 1.1079 ± 0.0009 | yes | no |
| 58 mol % DOPE/42 mol % Cholesterol (without freeze/thaw) | 175.7 | 0.112 | −66.77 ± 1.87 | 1.1108 ± 0.0021 | yes | no |
| Empty 58 mol % DOPC/42 mol % Cholesterol (with freeze/thaw) | 169.9 | 0.094 | 6.15 ± 7.62 | 1.0563 ± 0.0105 | yes | yes |
| Empty 58 mol % DOPC/42 mol % Cholesterol (without freeze/thaw) | 170.8 | 0.068 | 11.36 ± 2.41 | 1.0501 ± 0.0067 | yes | yes |
| Empty 58 mol % DOPC/42 mol % Cholesterol (with freeze/thaw) in 450 mg/mL Urea buffer | 169.7 | 0.114 | −2.21 ± 6.01 | 1.0869 ± 0.0052 | yes | no |
| 29 mol % DPPC/29 mol % DPPG/42 mol % Cholesterol (with freeze/thaw) | 178.0 | 0.091 | −66.80 ± 1.98 | 1.1045 ± 0.0007 | yes | no |

Example 5

Toxicity and Tolerability of Intravitreally Administered Urea

This Example provides an evaluation of the tolerability and toxicity of encapsulated urea after intravitreal (IVT) injection into the eyes of New Zealand white rabbits, as well as its efficacy for inducing PVD, and the settling pattern of intravitreally injected liposome constructs encapsulating urea.

Female New Zealand white rabbits were obtained from Western Oregon Rabbit Co. (Philomath, Oreg.) and were housed and cared for in compliance with the regulations of the USDA Animal Welfare Act and under the review and approval of the institution's Animal Care and Use Committee.

Prior to placement on study, each animal underwent an ophthalmic examination (slit-lamp biomicroscopy and indirect ophthalmoscopy). Ocular findings were scored according to a modified McDonald-Shadduck Scoring System (McDonald et al. "Eye Irritation," in Advances in Modern Toxicology: Dermatoxicology, at 579-582 (Marzulli et al. Eds., 1977)). The acceptance criteria for placement on study were scores of "0" for all variables.

Group 1 (Subgroups 1a, 1b, 1c): Acute/Urea Encapsulated Liposomes

Six female New Zealand White rabbits (two per subgroup) were administered urea-encapsulated liposome constructs (58 mol % DOPC, 42 mol % cholesterol) intravitreally (IVT) as a single dose into both eyes (OU). Animals were anesthetized with an intramuscular (IM) injection of ketamine hydrochloride (30 mg/kg), xylazine (5 mg/kg), and acepromazine (3 mg/kg) followed by isoflurane by inhalation (1-2.5%) in oxygen (1 L/min). One to two drops of topical proparacaine hydrochloride anesthetic (0.5%) were applied to the animal's eyes prior to the surgical procedure. Animals were kept anesthetized with their heads stabilized for three hours post dose, with one eye facing up and the other eye facing down.

After three hours, a clinical ophthalmic examination was performed, animals were euthanized. Vitreous humor (VH) was collected as 3 fractions. Pupils were dilated using one drop each of 10% phenylephrine and 1% tropicamide. Two 18G needles were inserted into the eye at the 3 o'clock and 9 o'clock position and advanced into the VH, one with the bevel pointed up towards the lens and the other with the bevel pointed down toward the retina. Three hundred μL of VH were drawn up through each needle, after which each needle was removed from the eye. The eye was then harvested and enucleated. Following enucleation, the remaining VH was collected as the third fraction. Samples from each eye in each animal remained separate and were not pooled. The weight of ocular tissues was recorded. Individual VH fractions were weighed separately. VH fractions were centrifuged at 16,100×g at room temperature for 20-30 minutes. The supernatant was separated. Pellets containing liposome constructs and supernatant were snap frozen separately on dry ice and stored at −60 to −80° C. Retina was also collected from these animals, snap frozen on dry ice, and stored at −60 to −80° C.

Group 2 (Subgroups 2a, 2b): Chronic/Free Urea

Two additional animals (one per subgroup) were administered a single or double dose of free urea solution IVT into the right eye (OD) and balanced salt solution (BSS) into the left eye (OS). Animals were anesthetized with an IM injection of ketamine hydrochloride (30 mg/kg) and xylazine (5 mg/kg). One to two drops of topical proparacaine hydrochloride anesthetic (0.5%) were applied to the animal's eyes prior to the surgical procedure.

Clinical ophthalmic examinations, fundus photography, and optical coherence tomography (OCT) were performed in these animals on Days 0-3, 4 (AM and PM), 8 (±1), 14, 21, and 28 post dose. For OCT, pupils were dilated with one drop each of 10% phenylephrine and 1% tropicamide approximately 10-15 minutes prior to imaging. Images were taken using the Spectralis® instrumentation (Heidelberg Engineering, Inc., Heidelberg, Germany).

The study design is summarized in Table 16.

ing revealed additional instances of PVD that were not revealed by clinical ophthalmic examinations. It can be concluded that PVD developed in the eyes of both animals treated with free urea solution within 2 days of dosing and persisted for the rest of the study, even if ophthalmic examinations and imaging did not always detect it. Because Group 1 animals did not undergo OCT imaging, instances of PVD after treatment with urea-encapsulated liposome constructs may have been undetected.

Fundus Photography

Both Subgroup 2a and Subgroup 2b animals exhibited clouding of the OD vitreous from Day 0 through Day 3. No such clouding was observed in the OS vitreous of either subgroup. The clouding was most likely an effect of vitreal protein changes due to the urea, as the cloudiness was not seen in the vehicle-treated eyes. Additionally, the cloudiness was likely not due to infection, as the vitreous in the urea-treated eyes began to clear after 3 days post dose.

Toxicity was observed at both doses. From Day 3 onward, the fundus imaging revealed severe retinal folding and vascular hemorrhage OD at the site of delivery (inferior nasal vitreal segment) in both Subgroups 2a and 2b. Again, this finding was not observed OS. The folding and hemorrhage peaked between Days 3 and 7 and then began to subside. By Day 29, there were some small but persistent regions of retinal folding, but the hemorrhaging was no longer detected in the fundus images. Given their selective

TABLE 16

| Group | Sub-group | Treatment | N | Encapsulated Urea Conc. (mg/100 μL) | Free Urea Conc. (mg/100 μL) | Total Urea Conc. (mg/100 μL) | Dosing Vol. (μL/eye) | Total Urea Dose (mg/eye) | Matrices Collected |
|---|---|---|---|---|---|---|---|---|---|
| 1 | 1a | Liposome constructs | 2 | 20 | 36 | 56 | 100 | 56 | Vitreous humor (N = 1) Retina (N = 1) |
|  | 1b |  | 2 | 40 | 36 | 76 | 100 | 76 | Vitreous humor (N = 1) Retina (N = 1) |
|  | 1c |  | 2 | 60 | 36 | 96 | 100 | 96 | Vitreous humor (N = 1) Retina (N = 1) |
| 2 | 2a | OD: Urea soln. | 1 | NA | 96 | 96 | 100 | 96 | NA |
|  | 2b | OS: BSS | 1 | NA | 96 | 96 | 200* | 192 |  |

OS: left eye;
OD: right eye;
OU: both eyes;
BSS: balanced salt solution;
IVT: intravitreal injection;
NA: not applicable
*Test or control articles were delivered as two 100 μL injections administered 34 (OD) or 35 (OS) minutes apart. Before the second injection, intraocular pressure was assessed to ensure that it had returned to a low enough value to permit the next injection.

Clinical Examination and Observation

No adverse effects on body weights and no severe adverse effects on general health were observed for animals receiving either urea encapsulated liposomes or free urea solution. In both groups of animals, ocular irritation and swelling were observed immediately after IVT injections that resolved over the next few days in animals survived past the dosing day.

Figure 7:
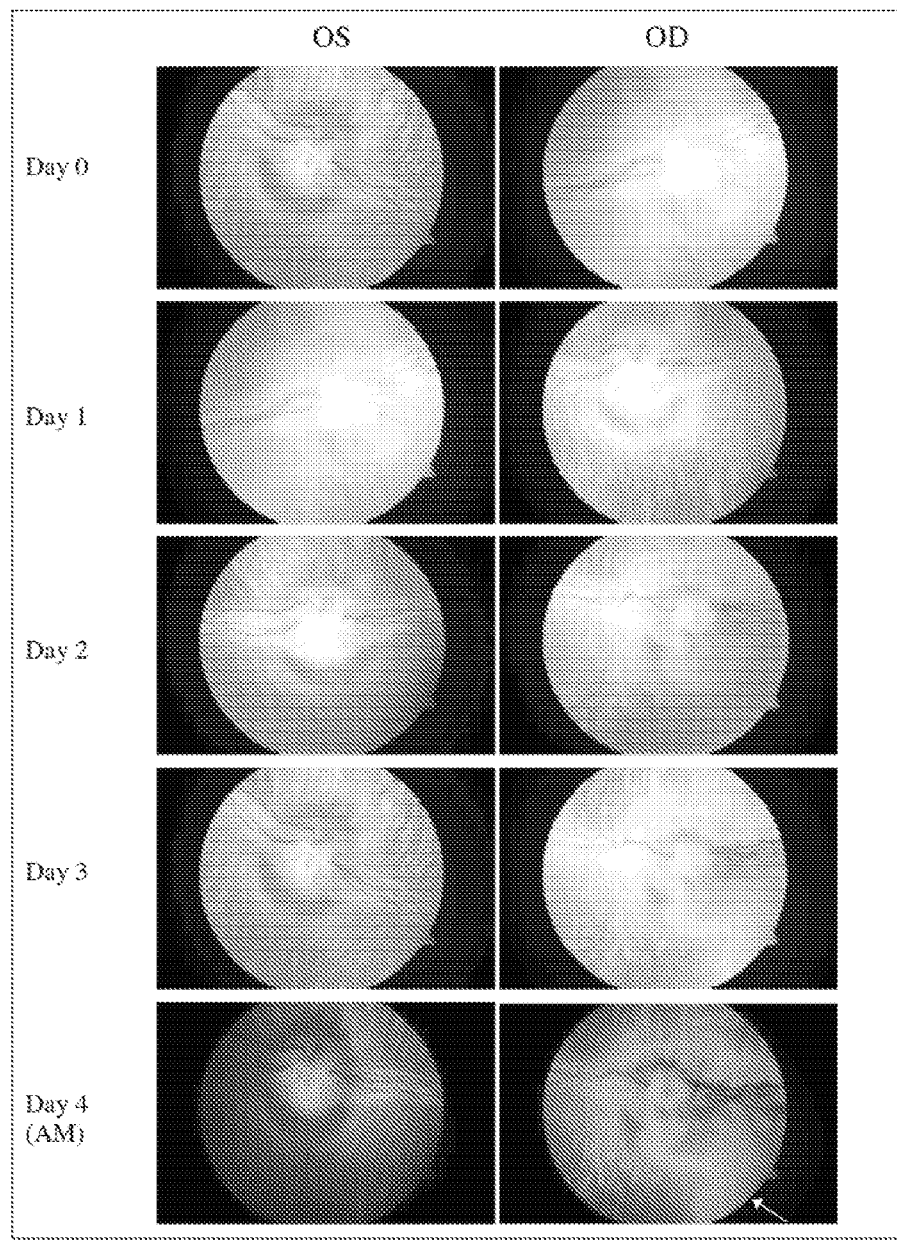
FIG. 7A-7B show representative fundus photographs of the Group 2a animal immediately post dose (Day 0), and on the indicated timepoints thereafter. The left eye (OS) received an intravitreal injection of balanced salt solution; the right eye (OD) received an intravitreal injection of 96 mg urea in solution. Hazy appearance of vasculature in the right eye is due to the presence of the drug product. Arrows in OD panels on days 4, 7, and 14 indicate drug product.
Figure 7:
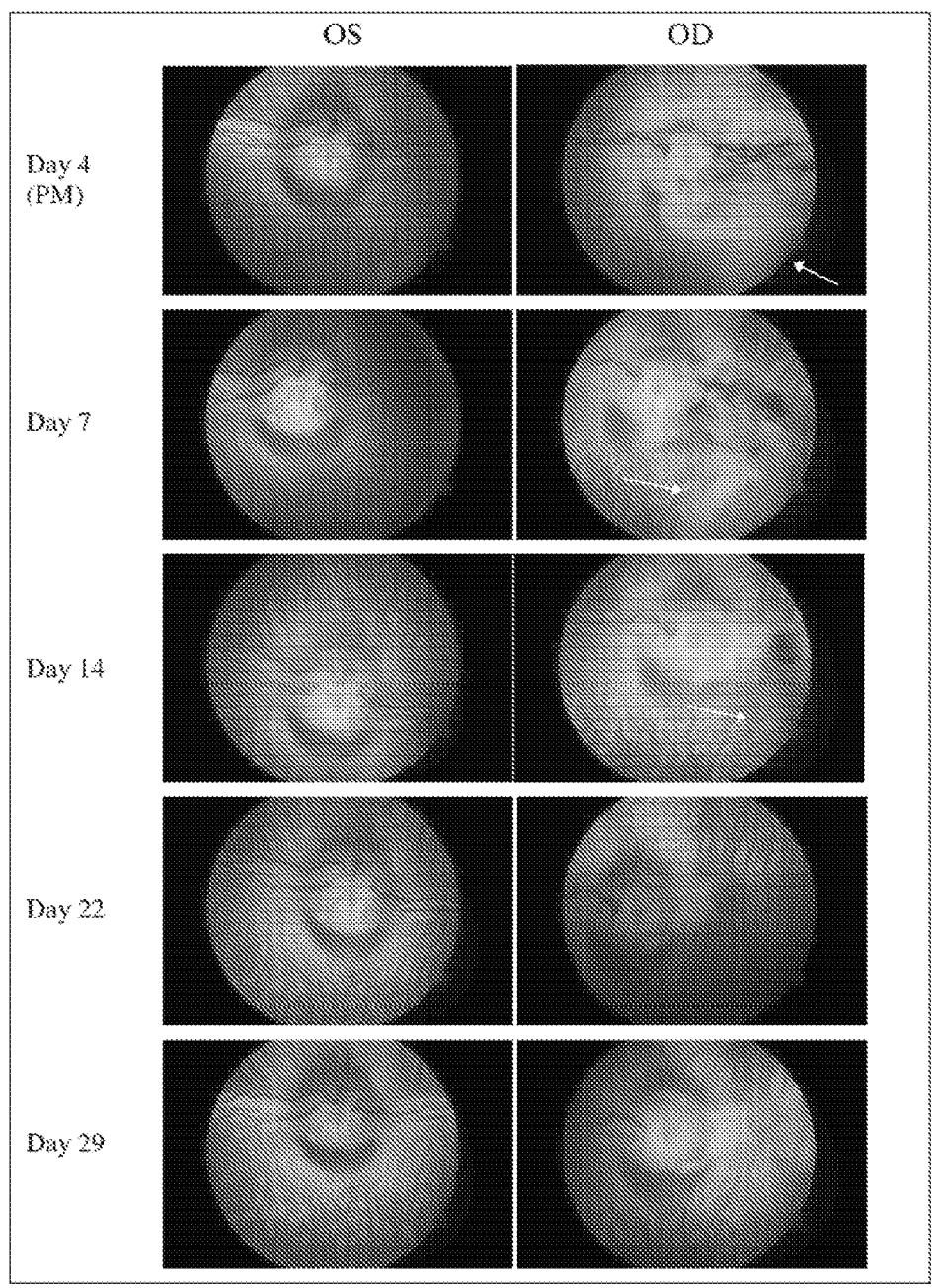

All animals had no ocular anomalies during the baseline pre-screening examination. Posterior vitreous detachment (PVD) was not observed during clinical ophthalmic examinations, with the exception of the Day 2 examination of both the Group 2a animal (free urea solution, single dose) and the Group 2b animal (free urea solution, double dose) in the treated right eyes (OD). However, PVD was not easily visible during clinical ophthalmic examinations; OCT imaglocalization and time course, both retinal folding and hemorrhage were likely urea-related. Representative images are shown in FIG. 7A-7B.

Optical Coherence Tomography

OCT imaging showed PVD in the right eye (OD) of the Subgroup 2a animal on Day 3. In the Subgroup 2b animal, PVD was observed OD on Days 4 (AM and PM), 7, and 14. No PVD was seen in in these animals OD at other imaging time points. However, because PVD is irreversible, it can be assumed that PVD was indeed present in both animals OD at all time points after Day 2, when PVD was noted OD in both animals during clinical ophthalmic examinations; most likely, OCT imaging on those days did not capture the regions exhibiting PVD. Neither animal exhibited PVD in the left eye (OS) at any time point.

OCT images also showed that the regions of retinal folding seen in the fundus imaging were areas where the retina had detached mostly at the ganglion cell layer and, in fewer cases, at the inner nuclear cell layer. The retinal detachment peaked between Days 3 and 7 and then began to subside, as reflected by retina re-attaching. Substantial numbers of hyper-fluorescent cells were observed in the retina after re-attachment, most likely indicating immune cell infiltration.

Figure 8:
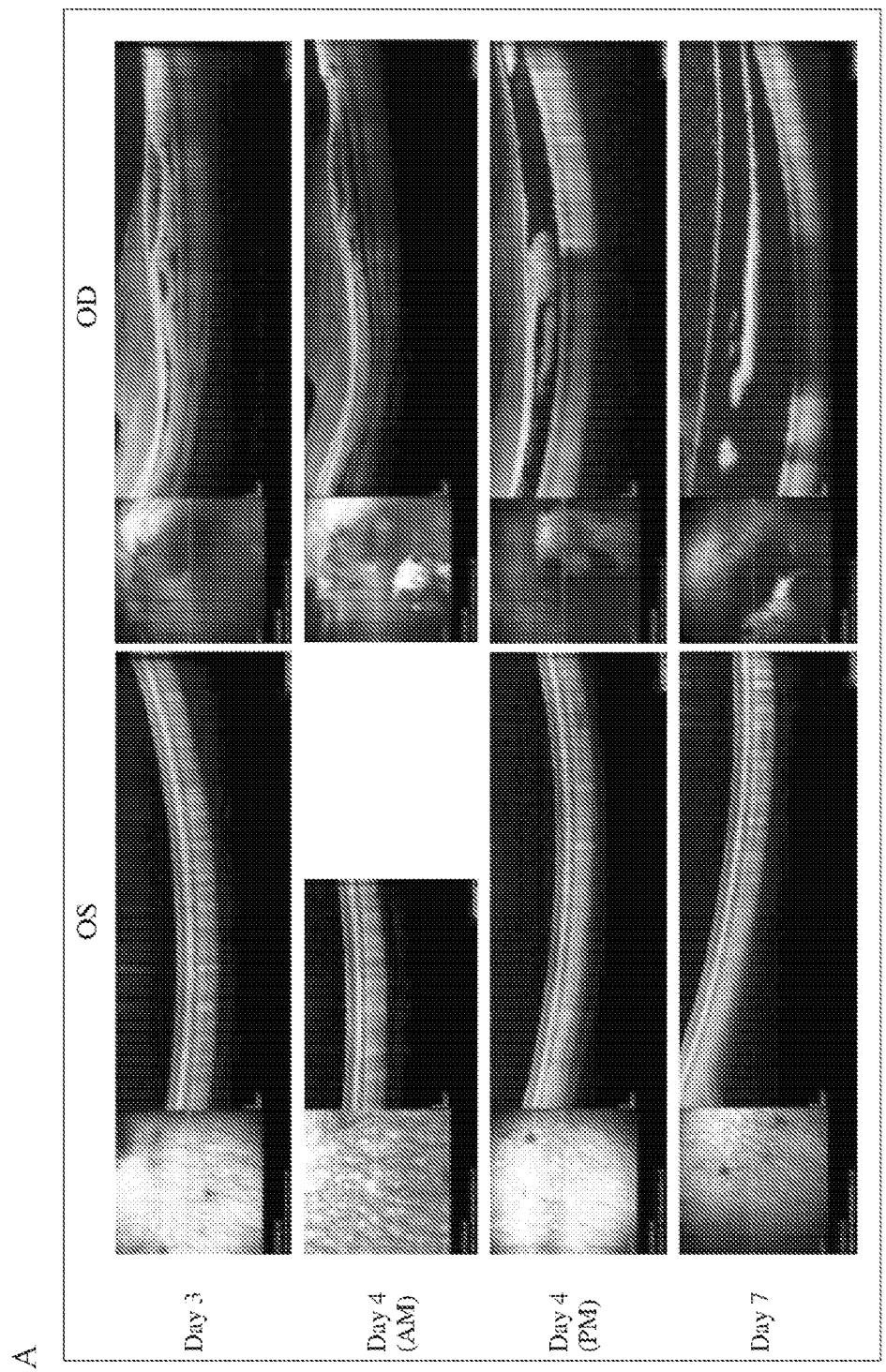
FIG. 8A-8B show representative optical coherence tomography (OCT) images of the Group 2b animal at the indicated post-dose timepoints. The corresponding fundus image is shown to the left of each sub-panel, with a green line indicating the position of the OCT image. The left eye (OS) received an intravitreal injection of balanced salt solution; the right eye (OD) received an intravitreal injection of 192 mg urea in solution.
Figure 8:
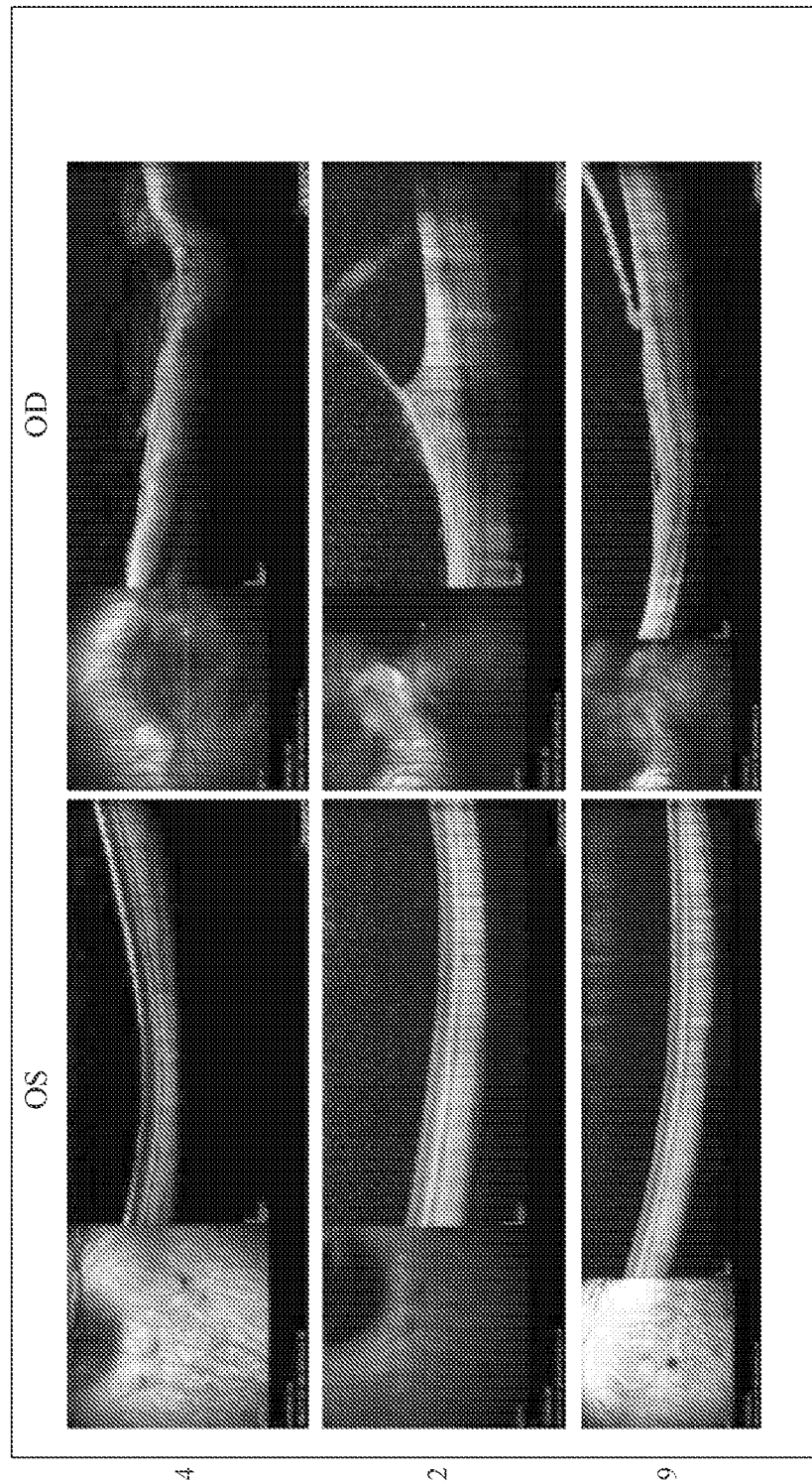

Representative images are shown in FIG. 8A-8B.

Example 6

Tolerability and Dose Response of Intravitreally Administered Free Urea

This Example provides an evaluation of the tolerability of reduced (compared to Example 5) concentrations of free urea after IVT injection into the eyes of New Zealand White rabbits (non-GLP), and a determination of the time it takes to induce a PVD after injection of each of the various dose strengths.

Five female New Zealand White rabbits were given a single administration of urea solution IVT into both eyes (OU) at doses of 2.5, 5, 10, 25 and 50 mg/eye.

Prior to placement in the study, each animal underwent an ophthalmic examination (slit-lamp biomicroscopy and indirect ophthalmoscopy). Ocular findings were scored according to a modified McDonald-Shadduck Scoring System. The acceptance criteria for placement on study were scores of "0" for all variables.

All procedures were performed using sterile technique. Animals were anesthetized for IVT injections, OCT, and B-Scan imaging with an IM injection of ketamine hydrochloride (50 mg/kg for imaging, 15-30 mg/kg for IVT injections) and xylazine (5 mg/kg). For one animal, anesthesia was prolonged via inhaled isoflurane (1-1.5% in 1.5-2 L/min oxygen) during baseline imaging due to extended duration of imaging. For another animal, inhaled isoflurane (2% in 1.5 L/min oxygen) was used to anesthetize the animal for IVT injections, because the animal had undergone baseline imaging (which included ketamine/xylazine anesthesia) earlier in the same day. One to two drops of topical proparacaine hydrochloride anesthetic (0.5%) were applied to the animal's eyes prior to the surgical procedure.

Prior to IVT injection, eyes were cleaned with Betadine and then rinsed with BSS. Using a ⅝ inch needle, injections were made 3 to 4 mm away from the limbus. Once the needle had been inserted, urea solution or BSS was injected. The needle was removed and the eye rinsed with BSS. Animals were recovered immediately after dosing and monitored during recovery. Triple antibiotic ophthalmic ointment was administered to the eyes during recovery.

The study design is summarized in Table 17.

Animals were euthanized on Day 35 (±4) and their eyes (whole globe) were collected and submitted for histopathological analysis.

Clinical Examination and Observation

General health observations were performed daily starting on Day 0, and body weights were recorded prior to dosing and prior to termination. All animals experienced mild weight loss over the course of the study. Weight loss may have resulted from the repeated anesthesia procedures, stress from repeated handling and restraint, or discomfort associated with the test article, or a combination of these factors. No other adverse effects of the drug and/or the study procedures on general animal health were observed.

Ophthalmic examinations (slit-lamp biomicroscopy and indirect ophthalmoscopy) were performed on Days −3 or 0 (baseline prior to test/control article administration), 1, 4, 7 or 8, 14, 21, and 35. Day 4 examinations were performed at the beginning of the workday. Day 21 examinations were performed only on Groups 1, 2, and 5. Ocular findings were scored according to a modified McDonald-Shadduck Scoring System. All animals had no ocular anomalies during the baseline pre-screening examination. Observations included assessment of the development and time course of PVD.

Dilated choroidal and/or retinal vessels were observed in all animals in one or both eyes at some or all clinical ophthalmic examination time points up to 21 days after administration. The dilatation was generally limited to the region of injection. As this finding was sometimes noted in both eyes, including the left eye (OS) injected with BSS only, it was likely a reaction to the IVT injection procedure, rather than an effect of the urea.

Mild conjunctival swelling in the Group 2 (10 mg/eye urea) animal and mild retinal hemorrhage around the injection site in the Group 5 (2.5 mg/eye urea) animal observed on the day after urea administration were likely due to the IVT injection procedure.

A ring-shaped opacity around the posterior lens capsule in the Group 4 (50 mg/eye urea) animal seen in the urea-treated right eye (OD) on the day after test article administration may have been due to irritation of the lens tissue by the high concentration of urea.

No evidence of PVD was noted during any of the examinations. PVD was difficult to visualize via clinical ophthalmic examinations; however, OCT imaging was able to identify cases of PVD (see below).

Fundus Photography

Images of the fundus were taken on Days −3 or 0 (baseline prior to drug or BSS administration), 1, 4, 7 or 8, 14, 21, and 35. Day 4 images were taken at the beginning of the workday. Day 21 images were taken only of Groups 1, 2, and 5. Animals were not anesthetized for imaging.

Figure 9:
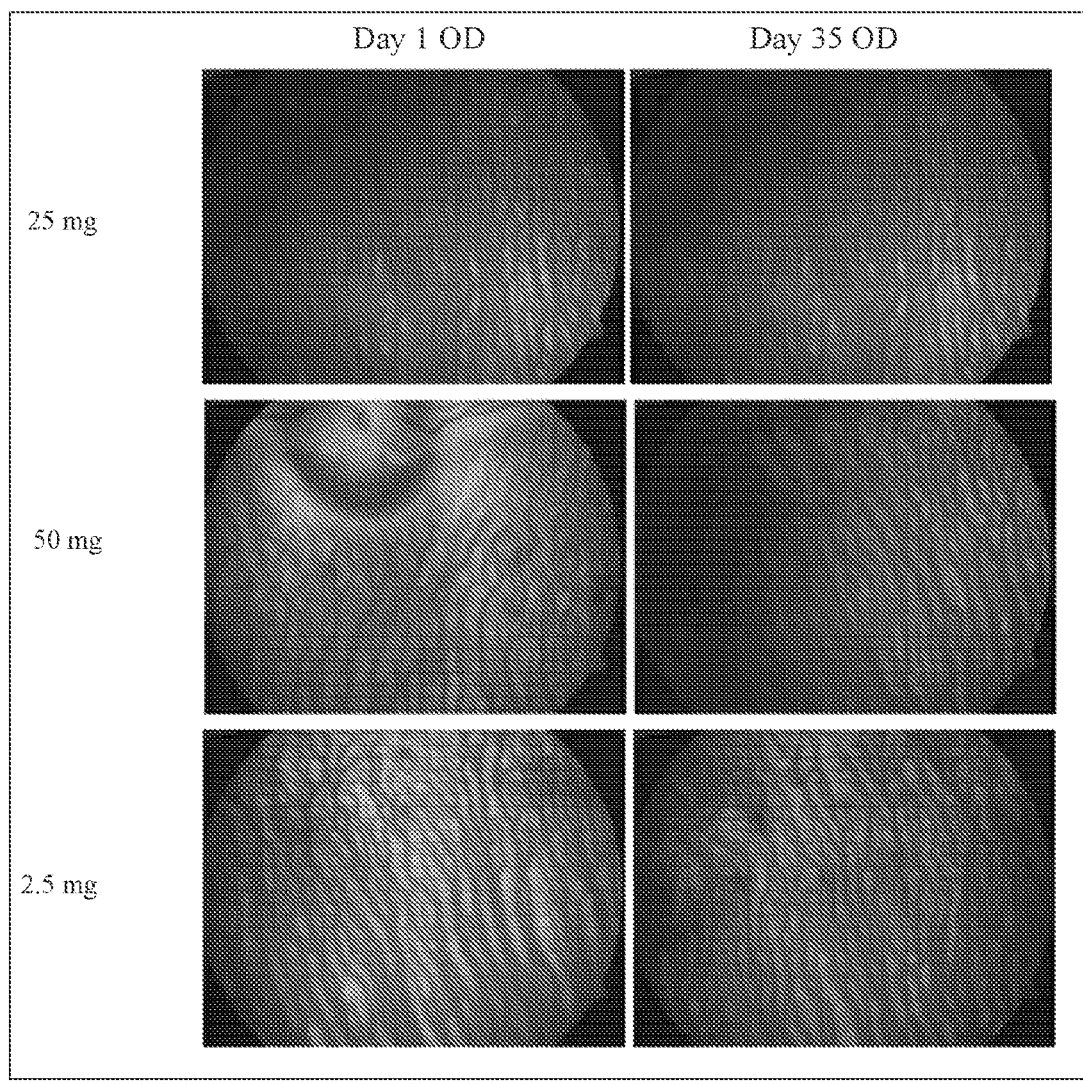
FIG. 9 shows representative fundus photographs of Group 3 (25 mg urea), Group 4 (50 mg urea), and Group 5 (2.5 mg urea) animals at 1 and 35 days after OD injection of urea solution.

Ocular abnormalities could not be observed in fundus images. Representative images are shown in FIG. 9.

TABLE 17

| Group | N | Treatment OD | Treatment OS | Route (OU) | Dose (mg/eye) | Volume (µL/eye) | Conc. (mg/mL) | Exams & Imaging |
|---|---|---|---|---|---|---|---|---|
| 1 | 1 | Urea Soln. | BSS | IVT | 5 | 50 | 100 | Baseline, Days 1, 4, 7 (±1), 14 (±1), 21 (±1), 35 (±4) |
| 2 | 1 | | | | 10 | 50 | 200 | |
| 3 | 1 | | | | 25 | 50 | 500 | |
| 4 | 1 | | | | 50 | 50 | 1,000 | |
| 5 | 1 | | | | 2.5 | 50 | 50 | |

Optical Coherence Tomography

OCT was performed on Days −3 or 0 (baseline prior to test/control article administration), 1, 4, 7 or 8, 14, 21, and 35. Day 4 images were taken at the beginning of the workday. Day 21 images were taken only of Groups 1, 2, and 5. Animals were anesthetized as described above. A total of 8 images per rabbit per day was acquired.

Retinal degradation, subretinal fluid, and signs of retinitis were observed in the OCT images of Group 3 and 4 animals starting the day after urea administration and in the Group 2 animal seven days after urea administration.

Figure 10:
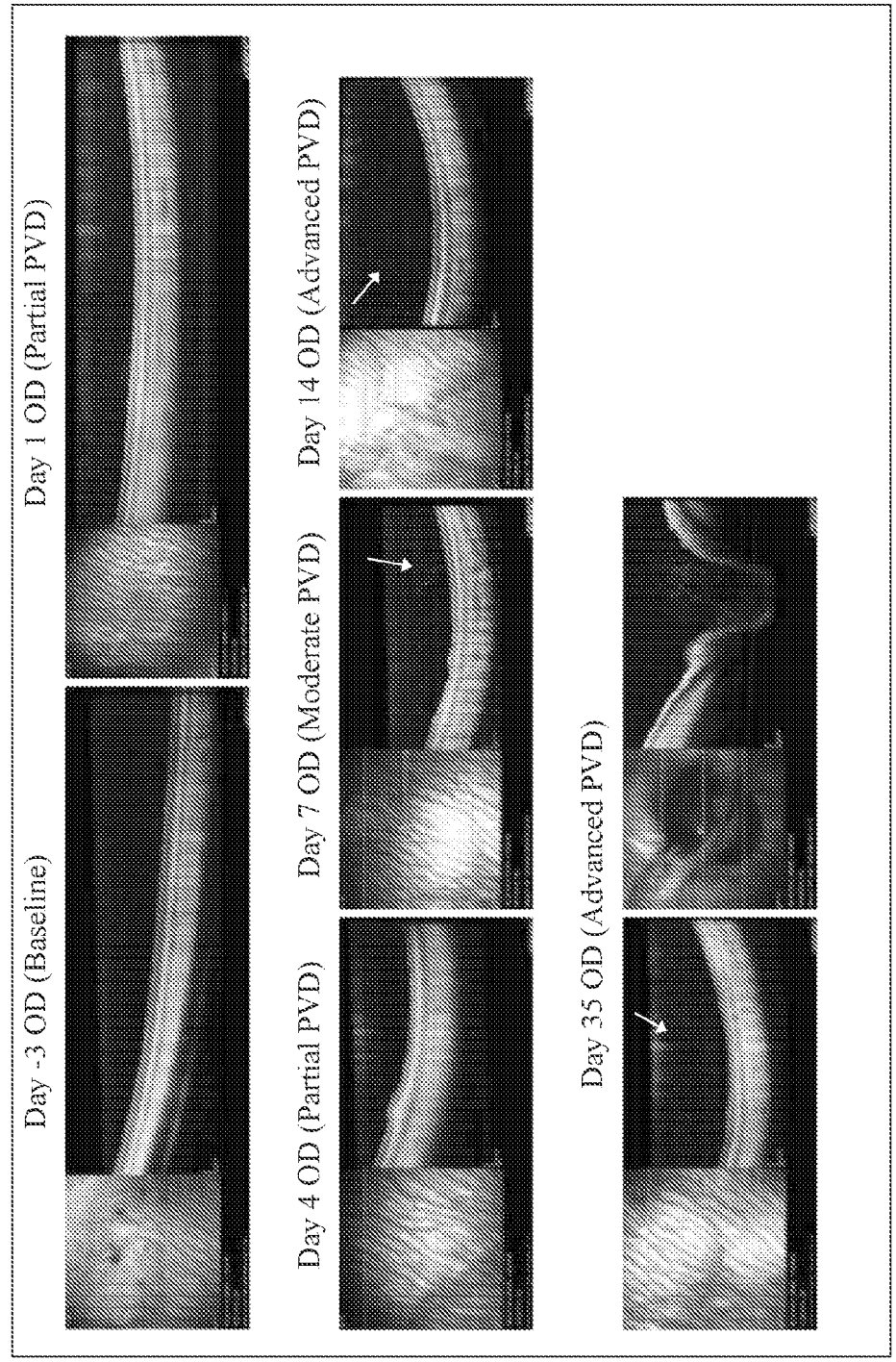
FIG. 10A-10B show representative OCT images of the Group 3 (25 mg urea) (FIG. 10A) and Group 4 (50 mg urea) (FIG. 10B) animals at the timepoints indicated. The corresponding fundus image is shown to the left of each sub-panel. Some instances of PVD are indicated by arrows.

OCT imaging revealed PVD in the treated eyes (OD), as described in Table 18. PVD was observed as a partial line of cellular components in the vitreous cavity with an underlying dark/black area with acellular components. Representative images are shown in FIG. 10A-10B.

TABLE 18

| Group | Urea Dose (mg) | Observations |
|---|---|---|
| 1 | 5 | Partial PVD on Day 35 |
| 2 | 10 | Partial PVD on Day 7 and beyond |
| 3 | 25 | Partial PVD on Day 1, moderate PVD on Days 4-7, moderate to advanced PVD on Day 14 and beyond |
| 4 | 50 | Partial PVD on Days 1-4, moderate PVD on Day 7, advanced PVD on Day 14 and beyond |
| 5 | 2.5 | Possible partial PVD on Day 4, none observed at later time points |

Higher urea concentrations were associated with earlier onset and more robust development of PVD; however, these concentrations also produced retinal degradation, subretinal fluid accumulation, and retinitis conditions in the treated eyes. Lower urea concentrations maintained retinal integrity, but were associated with partial and less robust PVD. No PVD and no retinal pathology were seen in the BSS-treated eyes (OS), confirming that both findings were likely urea-related.

All animals exhibited particles in the vitreous humor at some or all time points. Particles may have been pulled out of the retinal membrane into the vitreous humor by the injected urea. Particles in the optic nerve head were also seen in most animals at various time points. Observations of particles in the optic nerve head were likely incidental, as such particles are often observed even in the absence of ocular pathology; however, the presence of urea may have exacerbated this finding to some degree by further pulling particles into this region.

B-Scan Imaging

Figure 11:
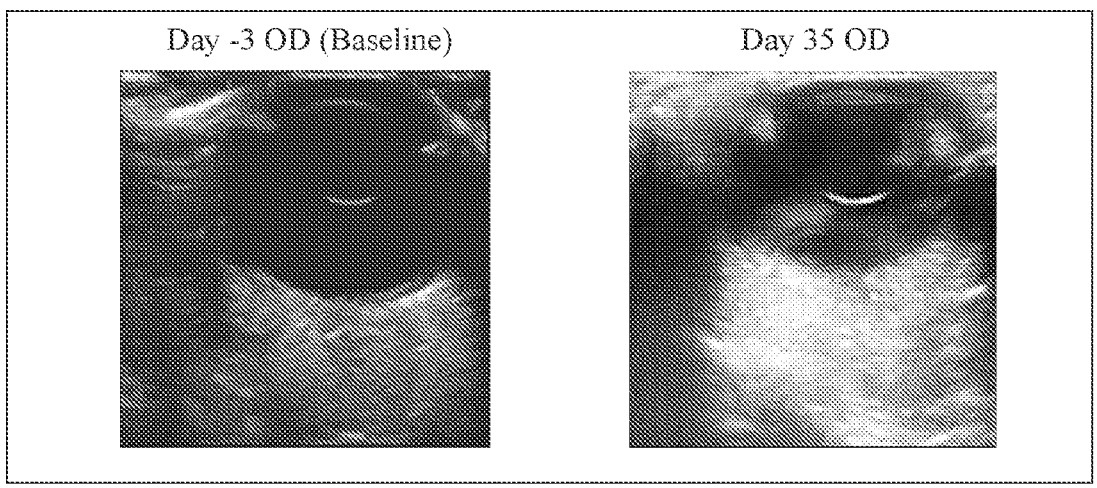
FIG. 11A-11B show representative B-scan images of Group 3 (25 mg urea) (FIG. 11A) and Group 4 (50 mg urea) (FIG. 11B) animals before and 35 days after OD injection of urea solution.
Figure 11:
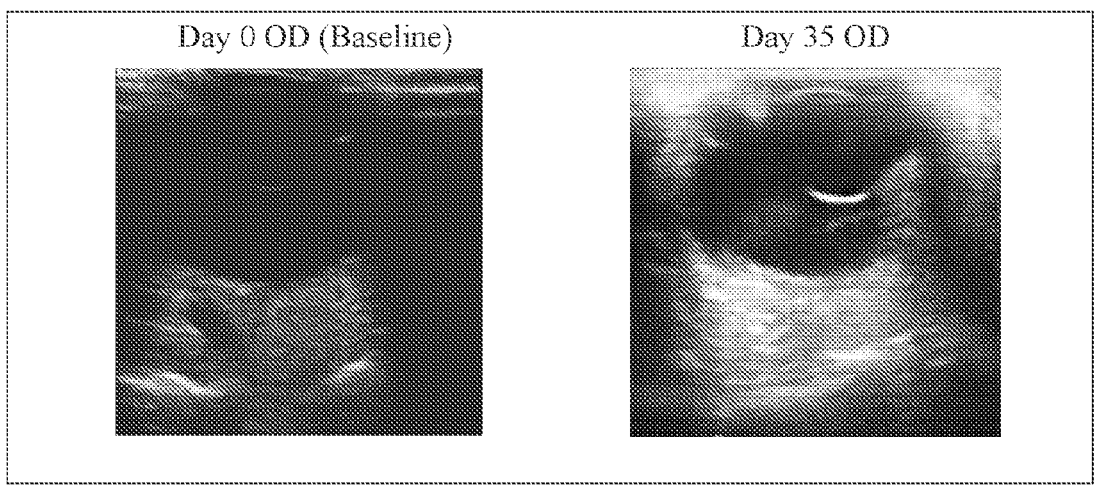

B-Scan ultrasound images were taken on Days −3 or 0 (baseline prior to test/control article administration) and on Day 35. Day 35 B-scan images of the Group 4 animal showed evidence of PVD in the right eye (OD), but not the left eye (OS). In B-scan images of other animals, no PVD could be detected. Representative images are shown in FIG. 11A-11B.

Histopathological Analysis

Histopathological analysis of the collected tissues found no evidence of adverse effects of urea or BSS on the eyes. PVD was difficult to conclusively assess during histopathological analysis, as separation of the vitreous humor from the retina can easily occur due to mechanical disruption during tissue handling and processing procedures.

Example 7

Localization and Effect of Liposome Constructs in Posterior Ocular Space

This Example provides observation of the physical location of liposome constructs in the posterior ocular space immediately after intravitreal injection of a wide range of dose concentrations and to evaluate the local effects of the drug following treatment.

Eight female New Zealand white rabbits were observed for 1 day or 32 days after a single intravitreous dose (Day 0) of a composition containing various concentrations of liposome-encapsulated and free urea. Liposomes were Formulation 2 (58 mol % DOPC, 42 mol % cholesterol). The study design is summarized in Table 19. Each group had an N of 1.

TABLE 19

| Group | Treatment* (Day 0, IVT, single dose, 50 μL/eye) | Ocular Evaluation (Dosed eye(s) only) | In-Life Assessment | Terminal Procedure |
|---|---|---|---|---|
| 1 | OD: Untreated OS: 20% Liposomes with Urea (3.5, 14) | OCT: pre-dose, 0.5 hr, 6 hrs, 24 hrs Photography**: 0.5 hr, 24 hrs | Clinical observations: once daily Body weight: pre-dose and end of study Food intake: qualitative, daily | Day 1: Eye globe collection and fixation for histopathology |
| 2 | OD: Untreated OS: 40% Liposomes with Urea (7, 15) | | | |
| 3 | OD: Untreated OS: 20% Liposomes with Urea (3.5, 14) | OCT: pre-dose, immediately post dose, 6 hrs, 24 hrs Retinal Imaging: pre-dose, immediately post dose, 24 hrs Photography**: immediately post dose, 6 hrs, 24 hrs | | |
| 4 | OD: Untreated OS: 40% Liposomes with Urea (7, 15) | | | |
| 5 | OD: 10% Liposomes with Urea (1.75, 10) OS: 10% Liposomes with Urea (1.75, 5) | OCT: pre-dose, 24 hrs, Days 4, 7, 14, 28 Retinal Imaging: pre-dose, immediately post dose, 24 hrs, Day 28 Photography**: immediately post dose, Days 1, 4, 7, 14, 28 | Clinical observations: once daily Body weight: pre-dose, weekly thereafter, and end of study Food intake: | Day 32: Eye globe collection and fixation for histopathology |
| 6 | OD: 20% Liposomes with Urea (3.5, 10) OS: 20% Liposomes with Urea (3.5, 5) | | | |

TABLE 19-continued

| Group | Treatment* (Day 0, IVT, single dose, 50 μL/eye) | Ocular Evaluation (Dosed eye(s) only) | In-Life Assessment | Terminal Procedure |
|---|---|---|---|---|
| 7 | OD: 40% Liposomes with Urea (7, 10) OS: 40% Liposomes with Urea (7, 5) | Ophthalmic Exam: pre-dose, Days 1, 7, 32 Electroretinography: Day 32 | qualitative, daily | |
| 8 | OD: 60% Liposomes with Urea (10.5, 5) OS: 60% Liposomes with Urea (10.5, 10) | | | |

*Urea concentrations shown as (mg encapsulated urea, mg free urea) per 50 μL product.
**Photography for test article residence inside eyes. Representative pre-dose pictures were taken as well.
OCT: optical coherence tomography;
OD: right eye;
OS: left eye During the in-life phase of the study, there were no obvious drug-related clinical observations, body weight changes, or abnormal food intake. Periodic ophthalmic examinations revealed vitreal cloudiness (Day 1, Day 7, and Day 32, presumably contributed by the drug), proteinaceous vitreal flare (Day 32) and vitreal cells (Day 32). These ophthalmic changes appeared to be generally dose-dependent.

OCT scans were taken via Bioptigen Envisu, high resolution fundus images were captured of the drug product location via the MicronX and a digital image of the dosed eyes was taken with an iPhone over the course of 32 days. Baseline images for all animals were obtained via OCT, MicronX and the digital camera. For Groups 1-4, treatment of the OS eye only allowed for animals to remain on their side with their eye facing upward and allowing the drug product to settle to the back of the eye.

PVD was observed in every treated eye with quicker response times with the higher concentration doses. The presence of particles (cloudiness) inside the vitreous chamber throughout the 4 weeks of study was generally confirmed by photography, retinal imaging, and OCT. In addition, after dosing, localized, irregularly shaped retinal layers (especially inner layers) were observed by OCT at all dose levels over the course of the study. The retinal changes occurred more likely in close proximity to vitreous areas with densely distributed particles.

Figure 12A:
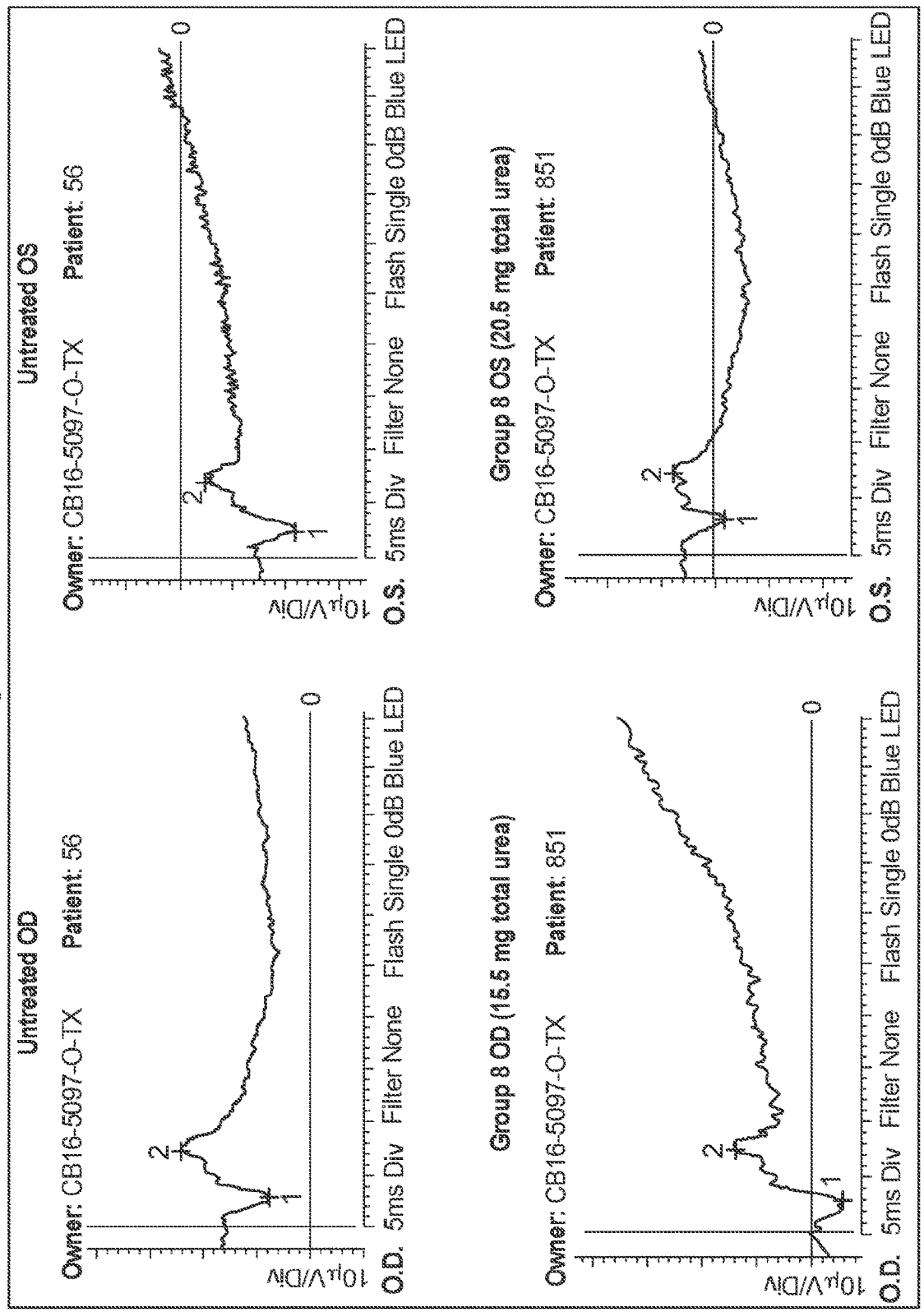
FIG. 12A-12B show Day 32 electroretinographs.
Figure 12B:
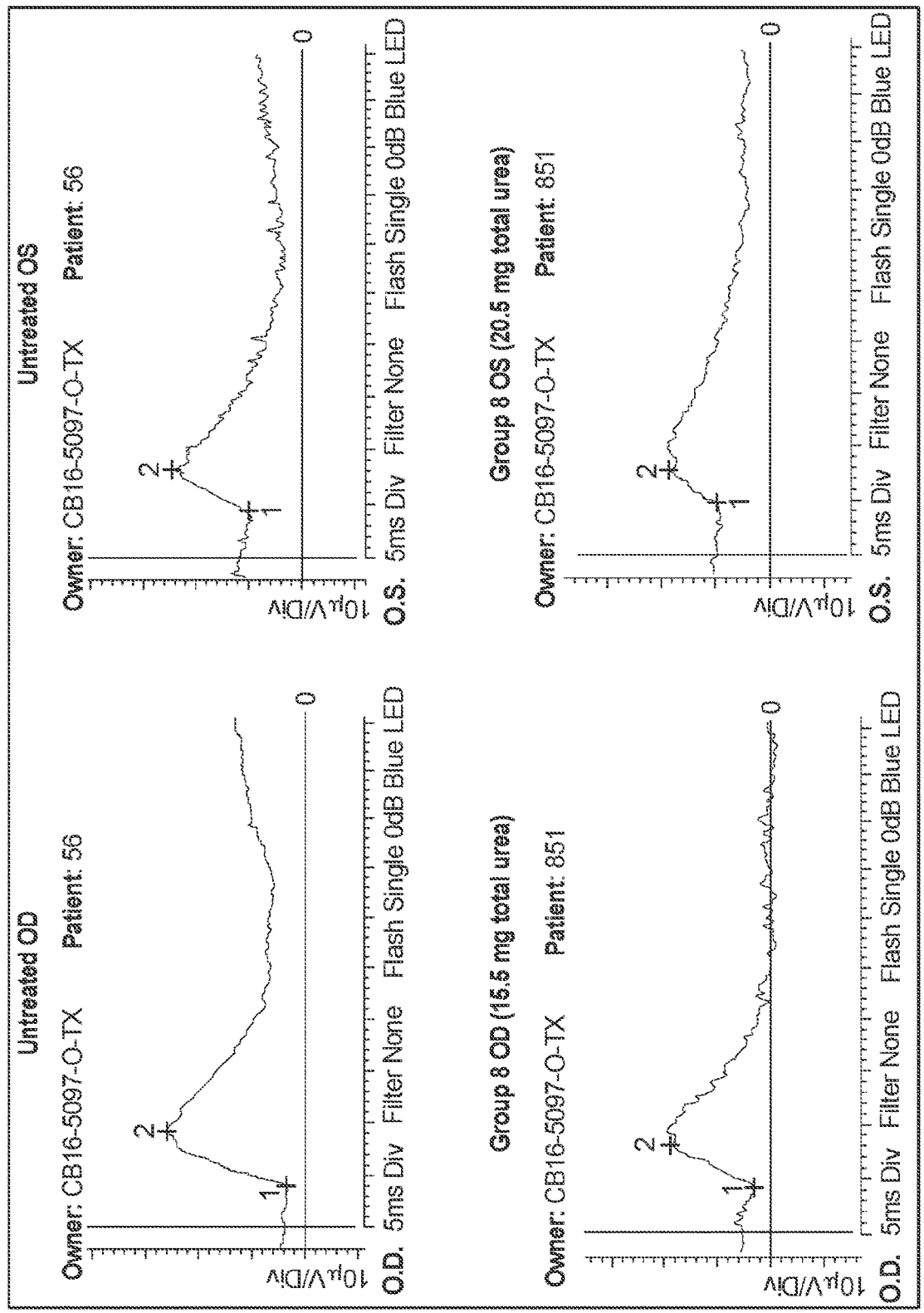

No obvious abnormal light-elicited electrical responses were observed in electroretinography (ERG) on Day 32, except that the eye with the highest liposome and urea concentrations (Group 8) showed lower amplitude of response (FIG. 12A-12B), which might indicate a reduction in photoreceptor function.

Largely consistent with the ophthalmic findings of vitreal cells, histopathological evaluation revealed inflammation (mild to severe, mostly mild) within posterior chamber. At least two complete sagittal sections of the entire globe were examined for each eye of all study animals. Particular attention was paid to the retina, optic nerve, vitreous, and anterior chamber. The relevant lesions consisted of acute inflammation, composed primarily of neutrophils, with a scattering of monocytoid cells, erthrocytes, and fibrin free in the posterior chamber, generally near the back of the chamber. Congestion, hyperemia, and some inflammation was also present in the superficial retina. Fine strands of vitreous were visible in all eyes and generally appeared to be detached from the retinal surface. These inflammatory changes were variable in severity and did not appear to be directly correlated with the concentration of the urea. Further, there was very little difference between the findings at Day 1 and Day 32. It would be logical to assume that increased urea concentration would correlate with inflammation severity, but this was not evident. This may be due to the very small group size. Vitreous separation from retina was found in all eyes of all groups. However, it is unclear whether they were related to the drug, since the separation can be a result of normal tissue processing.

The foregoing description of the specific embodiments of the present invention will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The present invention is further described by the following claims.

The invention claimed is:

1. A pharmaceutical composition comprising a liposome construct and a pharmaceutically acceptable carrier, wherein the liposome construct comprises an agglomerate of small unilamellar vesicles (SUVs); wherein the SUVs comprise a lamella consisting essentially of 58 mol % DOPC and 42 mol % cholesterol; wherein the SUVs comprise urea encapsulated within the SUVs; wherein the SUVs have a specific gravity that is greater than about 1.05, a z-average diameter of less than about 220 nm, and a polydispersity index value (PdI) of less than about 0.150, wherein a packed pellet of the SUVs comprises a concentration of encapsulated urea of at least about 200 mg per mL of packed pellet, wherein the pharmaceutically acceptable carrier comprises a concentration of unencapsulated urea to maintain equilibrium between the concentration of encapsulated urea and the concentration of unencapsulated urea, and wherein the composition is suitable for administration to the vitreous of a subject.

2. The pharmaceutical composition of claim 1, wherein the SUVs have a z-average diameter of less than about 200 nm.

3. The pharmaceutical composition of claim 1, wherein the SUVs have an encapsulation efficiency of at least 20%.

4. The pharmaceutical composition of claim 1, wherein the pharmaceutically acceptable carrier comprises 450 mg/mL urea.

5. The pharmaceutical composition of claim 1, wherein the composition comprises 40% SUVs and 60% pharmaceutically acceptable carrier (vol/vol ratio).

6. The pharmaceutical composition of claim 1, which is in the form of an emulsion.

7. The pharmaceutical composition of claim 1, which is in the form of a suspension.

8. A method for delivering urea to the vitreoretinal interface, the method comprising administering to the vitreous of a subject the pharmaceutical composition of claim 1.

9. The method of claim 8, wherein the administering is via intravitreal injection.

10. The method of claim 8, wherein the subject is in a supine position during administration of the pharmaceutical composition.

11. A method of inducing posterior vitreous detachment (PVD) in a subject having or susceptible to a disease or disorder of the macula or retina, the method comprising administering to the vitreous of the subject the pharmaceutical composition of claim 5.

12. The method of claim 11, wherein the administering is via intravitreal injection.

13. The method of claim 11, wherein the subject is in a supine position during administration of the pharmaceutical composition.

14. A method of treating diabetic retinopathy in a subject, the method comprising administering to the vitreous of the subject the pharmaceutical composition of claim 5.

15. The method of claim 14, wherein the administering is via intravitreal injection.

16. The method of claim 14, wherein the subject is in a supine position during administration of the pharmaceutical composition.

17. A pharmaceutical composition comprising a liposome construct and a pharmaceutically acceptable carrier, wherein the liposome construct comprises an agglomerate of small unilamellar vesicles (SUVs); wherein the SUVs comprise a lamella consisting essentially of 58 mol % DOPC and 42 mol % cholesterol and a surface modifying group; wherein the SUVs comprise urea encapsulated within the SUVs; wherein the SUVs have a specific gravity that is greater than about 1.05, a z-average diameter of less than about 220 nm, and a polydispersity index value (PdI) of less than about 0.150, wherein a packed pellet of the SUVs comprises a concentration of encapsulated urea of at least about 200 mg per mL of packed pellet, wherein the pharmaceutically acceptable carrier comprises a concentration of unencapsulated urea to maintain equilibrium between the concentration of encapsulated urea and the concentration of unencapsulated urea, and wherein the composition is suitable for administration to the vitreous of a subject.

18. The pharmaceutical composition of claim 17, wherein the surface modifying group is polyethylene glycol (PEG).

* * * * *